United States Patent
Druzgala et al.

(10) Patent No.: US 11,975,202 B2
(45) Date of Patent: May 7, 2024

(54) METHODS FOR REDUCING THE RISK OF STROKES BY PHARMACOTHERAPY TO REDUCE THE NUMBER AND DURATION OF ATRIAL FIBRILLATIONS

(71) Applicant: Xyra, LLC, Santa Rosa, CA (US)

(72) Inventors: Pascal Druzgala, Santa Rosa, CA (US); Peter Gerard Milner, Mountain View, CA (US)

(73) Assignee: Xyra, LLC, Santa Rosa, CA (US)

(*) Notice: Subject to any disclaimer, the term of this patent is extended or adjusted under 35 U.S.C. 154(b) by 0 days.

(21) Appl. No.: 18/222,621

(22) Filed: Jul. 17, 2023

(65) Prior Publication Data

US 2023/0355990 A1 Nov. 9, 2023

Related U.S. Application Data

(62) Division of application No. 17/978,835, filed on Nov. 1, 2022, now Pat. No. 11,759,640.

(60) Provisional application No. 63/334,852, filed on Apr. 26, 2022, provisional application No. 63/297,426, filed on Jan. 7, 2022.

(51) Int. Cl.
| | |
|---|---|
| A61N 1/36 | (2006.01) |
| A61B 5/361 | (2021.01) |
| A61N 1/362 | (2006.01) |
| G16H 40/67 | (2018.01) |

(52) U.S. Cl.
CPC ............ *A61N 1/3627* (2013.01); *A61B 5/361* (2021.01); *G16H 40/67* (2018.01)

(58) Field of Classification Search
CPC ....... A61N 1/3627; A61B 5/361; G16H 40/67
See application file for complete search history.

(56) References Cited

U.S. PATENT DOCUMENTS

| | | |
|---|---|---|
| 9,282,908 B2 | 3/2016 | Spector |
| 9,549,912 B2 | 1/2017 | Milner et al. |
| 11,759,640 B2 | 9/2023 | Druzgala et al. |
| 2011/0136779 A1 | 6/2011 | Milner et al. |

(Continued)

FOREIGN PATENT DOCUMENTS

WO 2021163331 A1 8/2021

OTHER PUBLICATIONS

Mischke, K., Knackstedt, C., Marx, N., & Vollmann, D. (2013). Insights into atrial fibrillation. Minerva medica, 104(2), 119-130.

(Continued)

*Primary Examiner* — Rex R Holmes
(74) *Attorney, Agent, or Firm* — Banner & Witcoff, Ltd.

(57) ABSTRACT

Disclosed are methods to treat patients with AFib by monitoring their heart rhythm to determine the presence and/or the number of episodes of long duration AFib, and optionally the extent of AFib burden. Patients who meet threshold requirements are qualified for the treatment of AFib with a dosage of budiodarone. Patient monitoring is continued in order confirm that the patient is and remains responsive to budiodarone therapy including dose adjusting the patient to achieve such therapy. Subsequently, monitoring is continued to confirm that the patient remains responsive. These methods allow for treatment of the AFib and, correspondingly, reduce or delay the risk of stroke and/or congestive heart failure in the treated patient.

20 Claims, 2 Drawing Sheets

(56) References Cited

U.S. PATENT DOCUMENTS

| | | |
|---|---|---|
| 2011/0144199 A1 | 6/2011 | Milner et al. |
| 2011/0269762 A1 | 11/2011 | Milner et al. |
| 2013/0143861 A1 | 6/2013 | Milner et al. |
| 2014/0309296 A1* | 10/2014 | Druzgala ............... A61K 9/08 514/469 |
| 2018/0028086 A1 | 2/2018 | Cao et al. |
| 2020/0323459 A1 | 10/2020 | Saha et al. |
| 2023/0233863 A1 | 7/2023 | Druzgala et al. |

OTHER PUBLICATIONS

Arya A, Silberbauer J, Teichman SL, Milner P, Sulke N, Camm AJ. A preliminary assessment of the effects of ATI-2042 in subjects with paroxysmal atrial fibrillation using implanted pacemaker methodology. EP Europace. 2009;11(4):458-64.

Capucci A, et al. Monitored atrial fibrillation duration predicts arterial embolic events in patients suffering from bradycardia and atrial fibrillation implanted with antitachycardia pacemakers. J Am Coll Cardioll 2005;46:1913-1920.

Ezekowitz MD, Nagarakanti R, Lubinski A, Bandman O, Canafax D, Ellis DJ, et al. A randomized trial of budiodarone in paroxysmal atrial fibrillation. Journal of Interventional Cardiac Electrophysiology. 2012;34(1):1-9.

Ezekowitz, M. D., Dimarco, J., Kaszala, K., Ellenbogen, K., Boddy, A., & Koren, A. A placebo-controlled, double-blind, randomized, multicenter study to assess the effects of dronedarone on atrial fibrillation burden in subjects with permanent pacemakers. J Interv Card Electrophysiol (2015) 42:69-76.

Glotzer, T. V. The Trends Study: is there a critical value of daily atrial tachyarrhytmia burden from device diagnostics that raises stroke risk. Circulation: Arrhythmia and Electrophysiology, vol. 2, Issue 5, Oct. 1, 2009: 474-480, https://ahajournals.org/doi/epub/1.1161/CIRCEP.109.849638.

Kirchhof P., Camm A. J., Goette A., Brandes A, Eckardt .L, Elvan A., et al. Early Rhythm-Control Therapy in Patients with Atrial Fibrillation. New England Journal of Medicine. 2020;383(14):1305-16.

Mischke, K.; Knackstedt, C.; Marx, N.; Vollmann, D. (Apr. 2013). "Insights into atrial fibrillation". Minerva Medica. 104 (2): 119-30. PMID 23514988.

Munger, T. M.; Wu, L. Q.; Shen, W. K. Journal of Biomedical Research. 2014, 28 (1): 1-17. doi:10.7555/JBR.28.20130191. PMC 3904170. PMID 24474959.

Perez M. V., Mahaffey K. W., Hedlin H., Rumsfeld J. S., Garcia A., Ferris T., et al. Large-Scale Assessment of a Smartwatch to Identify Atrial Fibrillation. New England Journal of Medicine. 2019;381(20):1909-17.

Wolf P. A, Abbott R. D., Kannel W. B. Atrial fibrillation as an independent risk factor for stroke: the Framingham Study. AHA Journals Stroke 1991; 22:983-988.

Zoni-Berisso, M.; Lercari, F.; Carazza, T.; Domenicucci, S. (2014). "Epidemiology of atrial fibrillation: European perspective". Clinical Epidemiology. 6: 213-20. doi:10.2147/CLEP.S47385. PMC 4064952. PMID 24966695.

Jun. 23, 2023—(WO) International Search Report and Written Opinion—App PCT/US2023/060238.

U.S. Appl. No. 18/221,235, filed Jul. 12, 2023.

PCT/US23/60238 filed Jan. 6, 2023.

PCT/US23/27521 filed Jul. 12, 2023.

Nov. 15, 2023—(US) Non-final Office Action—U.S. Appl. No. 18/351,261.

Nov. 14, 2023—(US) Non-final Office Action—U.S. Appl. No. 18/376,727.

U.S. Appl. No. 18/351,261, filed Jul. 12, 2023.

U.S. Appl. No. 18/376,727, filed Oct. 4, 2023.

* cited by examiner

METHODS FOR REDUCING THE RISK OF STROKES BY PHARMACOTHERAPY TO REDUCE THE NUMBER AND DURATION OF ATRIAL FIBRILLATIONS

CROSS-REFERENCE TO RELATED APPLICATIONS

This application is a divisional application of U.S. patent application Ser. No. 17/978,835, filed Nov. 1, 2022, which claims the benefit of U.S. Provisional Application No. 63/334,852, filed Apr. 26, 2022, and U.S. Provisional Application No. 63/297,426, filed Jan. 7, 2022, the entire contents of each of which is incorporated herein by reference.

FIELD

Disclosed are methods and devices for reducing the risk of strokes and/or congestive heart failure in patients diagnosed with paroxysmal or persistent atrial fibrillation (AFib) by determining whether a patient qualifies for, and then treating the patient with pharmacotherapy which reduces the number and/or duration of episodes of AFib.

STATE OF THE ART

AFib is a serious medical condition characterized by an abnormal heart rhythm often at accelerated heart rates. Untreated AFib leads to a significant increase in the risk of strokes, congestive heart failure, and death.

AFib has been categorized into at least three groups. Patients with intermittent episodes of AFib that last no more than 7 days before returning to normal, either on its own or with treatment, are defined as having paroxysmal AFib. Patients with intermittent episodes of AFib that last for more than 7 days before returning to normal are defined as having persistent AFib. Finally, patients who are constantly experiencing AFib are defined as having permanent AFib.

The underlying irregularity of the heart rhythm in AFib results in accumulation of blood in the upper chambers of the heart. The longer the blood remains in the upper chambers, the more likely that portion of the blood will coagulate and form clots. Once these clots leave the heart, they can enter the brain and cause strokes. In some cases, the blood clots cause transient ischemic attacks (TIAs) in the patient. Such TIAs can cause the patient to feel weakness on one side of the body, slurred speech, or impaired vision which is transitory in nature. In other cases, the blood clots cause debilitating strokes that can result in anything from a loss of functionality, such as speech or mobility, to a completely comatose state, or death.

In addition, AFib has been associated with not only an increased risk of stroke but also an increased risk of congestive heart failure—a serious debilitating condition that in the long term is terminal. The risk of stroke and/or congestive heart failure in patients with AFib is significantly higher than in those with a normal heart rhythm, and the risk increases with the duration and number of each episode of AFib (collectively the AFib burden). For example, the recent ENGAGE clinical trial evaluated the risk of stroke for patients, which is set forth in Table 1 below:

TABLE 1

| normal heart rhythms | ~1% per year | % increase over normal |
|---|---|---|
| paroxysmal heart rhythms | ~1.49% per year | 49% |
| persistent heart rhythms | ~1.83% per year | 83% |
| permanent heart rhythms | ~1.95% per year | 95% |

Recent studies have shown that an increase in the risk of stroke and/or congestive heart failure is independent of whether the patient is symptomatic or asymptomatic for AFib. See, for example, Flaker, et al., Asymptomatic Atrial Fibrillation: Demographic Features and Prognostic Information from the Atrial Fibrillation Follow-Up Investigation of Rhythmic Management (AFFIRM) Study, American Heart Journal, April 2005, pages 657-663 which is incorporated herein by reference in its entirety. Stated differently, recognition by the patient of periodic AFib episodes does not mean that the risk of stroke or congestive heart failure has been reduced or removed.

In addition, there is a recognition that long duration episodes of AFib (i.e., AFib episodes that last 1 hour or more) carry an increased risk of stroke, which increases as the duration of these episodes increases. The longer the duration of the episode, the higher the risk of a stroke. Accordingly, AFib episodes greater than one hour are designated as "long duration" episodes. Still further, such long duration episodes are divided into two subsets: "medium-long duration" episodes, which are from about 1 hour to about 24 hours or less in duration, and "longer-duration" episodes which are longer than about 24 hours in duration, but not permanent AFib. However, not all patients suffering from paroxysmal AFib or persistent AFib will evidence long duration AFib. Indeed, the AFib burden is related to, but distinct from, medium-long or longer-duration AFib. For example, patients with a low AFib burden may experience episodes of long duration AFib, albeit on an infrequent basis. Likewise, patients with a higher AFib burden may experience multiple short duration episodes of AFib, but little or no long duration episodes. The ability to distinguish between AFib burden and long duration AFib is essential to address the risk of stroke, congestive heart failure, and the like. This is particularly important to an attending clinician who must evaluate the efficacy of pharmacotherapy designed to reduce the number and duration of AFib episodes.

Several drugs are designed to treat AFib, including beta blockers and calcium channel blockers. Many of these drugs are designed to control heart rates rather than controlling heart rhythm. However, the risk of stroke is related to extended episodes of AFib, and not the underlying heart rate. Recently, budiodarone (disclosed in U.S. Pat. No. 9,549,912, which is incorporated by reference in its entirety) has been shown to control heart rhythm and significantly reduce episodes of long duration AFib. However, because not all patients with AFib evidence episodes of long duration AFib, administration of such a heart rhythm drug to just any patient who experiences AFib is not recommended. Even for those patients with medium-long duration and/or longer-duration episodes of AFib who are being treated with budiodarone, the extent of reduction in AFib episodes is dose-dependent and variable from patient to patient due to the age, sex, weight, extent of disease progression and other factors known in the art. In addition, as with other pharmacotherapy treatments, there will invariably be patients who do not respond.

While there are many wearables available that can diagnose the presence of AFib in a patient including watches, Holter monitors, patches, and the like, the ability to simply diagnose is different from the ability to continuously assess the presence of long duration AFib in patients suffering from paroxysmal or persistent AFib. Continuous monitoring of a patient's heart rhythm is now possible with wearables such as patches and/or devices. The latter includes wireless transmission devices (such as MCOT (mobile cardiac outpatient telemetry) sold by Phillips BioSciences, Best, Netherlands) that allow for seamless collection of a patient's heart rhythm data. To date, such devices have been primarily used in naïve patients suspected of having AFib, and as such, have primarily been used for diagnosis. Currently, there are no examples where these devices should or could be used in combination with pharmacotherapy to assess responsive and non-responsive patients to drugs that are designed to reduce long duration episodes of AFib. This would include enabling the clinician to monitor the disease progression and/or regression in a treated patient and dose-adjusting the amount of drug to achieve an initial therapeutic result or dose-adjusting the patient to regain or maintain a therapeutic result at the lowest possible dose.

As such, clinicians are typically left with only minimal short-term data of up to about 2 weeks or so regarding a patient's heart rhythm over this span. Such limited data can blind the clinician to conditions where sporadic episodes of AFib occur infrequently but are of long duration which can be easily missed using only short-term data. Moreover, and perhaps more seriously, many diagnostic devices are not compatible with monitoring and/or pharmacotherapy. This is because the diagnosis requires short-term monitoring whereas pharmacotherapy requires continuous long-term monitoring of the patient by the clinician to assess whether the prescribed drug is effective in reducing both the number of long duration episodes of AFib as well as reducing the patient's AFib burden.

Thus, there exists an ongoing conundrum; how can the clinician consider pharmacotherapy with a drug such as budiodarone to reduce both AFib burden and long duration episodes of AFib if the clinician is unaware of the long-term values for either metric in the patient? Moreover, if the clinician does prescribe this drug, how can the clinician know if the dosing of the drug is effectively reducing the episodes of long duration episodes of AFib? In the absence of such information, the clinician will likely protect the patient by prescribing a blood thinner such as rivaroxaban (Xarelto®) which reduces clotting arising from AFib. However, the use of such blood thinners comes with a price. For example, the Market Insider reported that the use of Xarelto lead to over 15,000 adverse events in 2016 alone. See, for example, Report: More than 15,000 Adverse Events Linked to Xarelto in 2016, https://markets.businessinsider.com/news/stocks/report-more-than-15-000-adverse-events-linked-to-xarelto-in-2016-1002203317 (last accessed Oct. 28, 2022).

In view of the above, there is an ongoing need to improve the monitoring of patients such that the clinician can accurately quantify the number and duration of long duration episodes of AFib in a patient as well as the AFib burden. There is a further need to correlate those patients with long duration AFib, including medium-long or longer-duration AFib, as being suitable for treatment with budiodarone and potentially create a registry of such patients. Still further, there is a need to allow the clinician to determine, directly or indirectly, whether the dosing of budiodarone is effective thereby allowing the clinician to adjust the dosing as appropriate or to remove a non-responsive patient from budiodarone therapy.

SUMMARY

Disclosed are methods and devices useful in qualifying patients with symptomatic or asymptomatic paroxysmal or persistent AFib with treatment with an antiarrhythmic drug, such as budiodarone. Such treatment is designed to reduce or eliminate the risk of stroke or congestive heart failure in a patient evidencing episodes of long duration AFib as well as a threshold level of AFib burden. In particular, the methods and devices described herein allow for continuous or semi-continuous monitoring of such a patient's heart rhythm to assess the AFib burden for such patients as well as the duration of such episodes. This allows a clinician to evaluate a patient to determine whether that patient so monitored has a requisite number of episodes of long duration AFib as well as a threshold level of AFib burden. Patients meeting such criteria are deemed "qualified" candidates for starting therapy with budiodarone.

Patients already ascertained by conventional means, such as a Holt monitor, as having episodes of long duration AFib and above threshold levels of AFib burden are preferably monitored as above before being placed on budiodarone to assess a baseline number and duration of the episodes of long duration AFib as well as AFib burden to determine whether subsequent pharmacotherapy is efficacious. In any event, all qualified patients placed on budiodarone therapy are maintained on monitoring after the start of therapy. Such continued monitoring allows the clinician to evaluate the efficacy of the drug for that patient. In essence, the methods disclosed herein provide for pharmacotherapy with budiodarone as a form of personalized medicine where the severity of the disease in a qualified patient is matched with an appropriate dose of budiodarone that is minimally efficacious for that patient—or if the patient is a non-responder, the patient is disqualified from budiodarone therapy. The methods disclosed herein avoid the use of excessive amounts of budiodarone in treating AFib while understanding that some patients require more budiodarone than others to achieve therapy. Still further, the ability to remove a non-responder from therapy represents a new paradigm in treatment by limiting therapy to those patients who are responders.

In one embodiment, the overall efficacy of budiodarone in a cohort of patients can be improved by limiting the continued administration of the drug to those patients evidencing a therapeutic result. In one instance, qualified patients are those who have been previously identified or confirmed to meet minimum thresholds. Qualified patients who show efficacy with budiodarone, either initially and/or after dose adjustments, are continued on the therapy whereas those patients who lack such efficacy (non-responders) are removed from the therapy. Given the variability of the underlying AFib burden as well as the number of long duration AFib episodes in a cohort of patients, budiodarone is efficacious in a significant number of patients, but likely not all patients. Using the methods and devices described herein in combination with budiodarone therapy, the clinician is able to ascertain whether a given patient qualifies for budiodarone therapy and/or whether that therapy is providing efficacious results, thereby allowing the clinician the ability to maintain therapy for only those patients who benefit from budiodarone treatment and at a minimal dose that is needed to achieve efficacious results.

The above represents a significant advancement in the treatment of symptomatic and asymptomatic paroxysmal or persistent AFib in patients who may or may not have episodes of long duration AFib and/or who may or may not obtain efficacious results with budiodarone. Such is not possible by protocols that are limited to diagnosis.

By using the wearables described herein, the clinician can qualify only those patients with paroxysmal and/or persistent AFib who evidence threshold levels of long duration episodes of AFib and/or AFib burden for treatment with budiodarone. Still further, the clinician can then monitor these patients to assess whether the patient's AFib is responsive to such treatment or whether dose adjustment of budiodarone is warranted. Finally, the clinician can also remove non-responsive patients from such therapy. Such represents a solution to a long felt need in the art—namely how to control long-duration AFib to reduce the risk of stroke or congestive heart failure.

Optionally, such qualifying patients can be placed on a national registry that enables the clinician to prescribe budiodarone solely to such registered patients. Patients who show efficacy with budiodarone, either initially and/or after dose adjustments, are retained on the registry, whereas patients who lack such efficacy are removed from the registry.

The devices (wearables) described herein address a critical gap in generating the information to allow a clinician to properly evaluate the long-term heart rhythm of a patient, especially as it relates to assessing the patient's AFib burden and the number and duration of long duration episodes of AFib, before and/or after the start of budiodarone therapy. Still further, the continued availability of such information after initiation of therapy allows the clinician to dose-adjust the amount of budiodarone administered to reach a desired therapeutic result at a reduced effective dose (e.g., the minimum effective dose). Still further, these methods and/or devices will elicit patient participation through self-monitoring, which is a well-accepted way of improving patient compliance with their drug regimen. This, in turn, will reinforce the long-term efficacy of any antiarrhythmic drug treatment in reducing or eliminating long-term risks of stroke.

In one embodiment, a wearable is engageable and disengageable by a patient, who may be diagnosed with paroxysmal AFib or persistent AFib. The wearable may comprise and/or be configured to receive data from at least one electrode and/or optical sensor that, when the wearable is engaged, continuously or semi-continuously monitors the patient's heart rhythm. The wearable may also, or alternatively, comprise a processing unit (e.g., a processor, a central processing unit (CPU), a microprocessor, a digital signal processor, a computing device, and the like) that is configured to collect and optionally evaluate the heart rhythm data to determine the presence of and/or number of long duration episodes of AFib. The processing unit may also, or alternatively, be configured to store the heart rhythm data. The wearable may also, or alternatively, comprise a transmission component (e.g., a transmission device) that is configured to access the data in the processing unit (e.g., wirelessly and/or via circuitry that connects the transmission component and the processing unit). The transmission component may be capable of initiating a communication directly or indirectly to a computing device accessible by the patient and/or a clinician and/or another caregiver of the patient, wherein the communication may provide the heart rhythm data and/or data resulting from evaluating the heart rhythm data.

In another embodiment, a method for monitoring a patient treated for AFib for one or more long duration episodes of AFib may include engaging an engageable and disengageable wearable. The wearable may comprise at least one electrode or optical sensor that can continuously or semi-continuously monitor a heart rhythm. The wearable may comprise a transmission device and/or circuitry that connects the at least one electrode or optical sensor and the transmission device. The wearable may also or alternatively, comprise a CPU that can collect the heart rhythm data, evaluate said data for the presence of long duration episodes of AFib; and store the data. The method may further comprise communicating to the patient and/or the patient's caregiver the heart rhythm data, which may enable the caregiver to analyze one or more long duration episodes of AFib.

In another embodiment, a method may be a method for reducing risk of one or more of: transitioning from paroxysmal AFib to persistent AFib in a patient with paroxysmal AFib; transitioning from persistent AFib to permanent AFib in a patient with persistent AFib; or stroke in a patient with AFib, wherein the patient is being treated with budiodarone and the treatment may have reduced and/or inhibited episodes of long duration AFib. The method may include evaluating heart rhythm data collected by a wearable engaged by the patient. The wearable may comprise at least one electrode or optical sensor that can continuously or semi-continuously monitor a heart rhythm. The wearable may comprise a transmission device and/or circuitry that connects the at least one electrode or optical sensor and the transmission device. The wearable may also or alternatively, comprise a CPU that can collect the heart rhythm data, evaluate said data for the presence of long duration episodes of AFib; and store the data. The method may further comprise adjusting the dose of budiodarone to reduce further episodes of long duration AFib (e.g., as deemed necessary by a clinician), thereby reducing the risk of the one or more of the transitioning from paroxysmal AFib to persistent AFib, the transitioning from persistent AFib to permanent AFib, and/or the stroke.

In another embodiment, a system may comprise a wearable that collects heart rhythm data from a patient diagnosed with either paroxysmal AFib or persistent AFib, a CPU that is in communication with the wearable and that can collect and/or store the data, and a transmission device that can communicate with the CPU and that can send the data to one or more designated recipients.

In another embodiment, a method may be for reducing the risk of stroke or congestive heart failure in a patient with paroxysmal AFib and/or persistent AFib and being treated with a pharmaceutical. The method may comprise obtaining the patient's heart rhythm data from a wearable engaged by the patient, wherein the wearable may comprise at least one electrode or optical sensor that can continuously or semi-continuously monitor heart rhythm, a transmission device capable of initiating transmission of data, circuitry connecting the at least one electrode or optical sensor and the transmission device, and a CPU configured to collect and store the heart rhythm data. The method may further comprise evaluating said heart rhythm data to determine the effectiveness of the pharmaceutical by correlating the presence and/or absence of episodes of long duration AFib to the dose of the pharmaceutical, determining whether the dose of the pharmaceutical is effective or ineffective in reducing or eliminating episodes of long duration AFib in the patient; and, if ineffective, increasing the dose one or more time, until said dose is effective, thereby reducing the risk of stroke or congestive heart failure.

In one embodiment, the wearable is programmable (e.g., by a clinician). In one embodiment, the wearable is programmed to transmit all heart rhythm data and/or only that data of long duration episodes of AFib.

For the purposes of this disclosure, any episode of AFib that has a duration of at least 1 hour is considered a "long duration" episode. However, for clarity, long duration episodes include a subset of episodes that are further defined as being of "medium-long duration". Such medium-long duration episodes range from at least about 1 hour to no more than about 24 hours. Episodes of AFib that range from more than about 24 hours but are not permanent are categorized as longer-duration episodes. These subsets will allow the clinician to better evaluate the benefits of budiodarone therapy, e.g., when patients with a history of long-duration episodes of AFib transition to experiencing a greater percentage of medium-long duration episodes instead of longer duration episodes.

In one embodiment, the medium-long duration episodes of AFib range from about 1 hour to about 24 hours, and, in another embodiment, such medium-long duration episodes of AFib range from at least 5 hours up to about 24 hours in duration.

In one embodiment, when a first set of collected data is transmitted out of a computing device, such as a central processing unit (CPU), that data is discarded from the CPU so that th new data can be collected.

In one embodiment, there is provided a method to assess whether a patient with paroxysmal or persistent AFib qualifies for budiodarone therapy which method comprises:
  a) selecting a patient afflicted with paroxysmal or persistent AFib having an unknown AFib burden and/or unknown number of episodes of long duration AFib over a set period of time;
  b) fitting said patient with a wearable wherein said wearable comprises:
    i) at least one electrode and/or optical sensor that, when the wearable is fitted, is continuously or semi-continuously monitoring the patient's heart rhythm;
    ii) a CPU that collects and stores the heart rhythm data; and
    iii) a transmission component that connects to the data in the CPU, wherein said transmission component is capable of initiating a communication directly or indirectly to a clinician wherein said data is optionally stored;
  c) collecting and transmitting the heart rhythm data directly or indirectly to said clinician who evaluates the data for the presence and number of medium-long and/or long-duration episodes of AFib and the extent of AFib burden;
  d) qualifying said patient for budiodarone therapy if said data evidence the requisite number of episodes of long duration AFib and a requisite AFib burden.

In one embodiment, the CPU is also capable of evaluating the stored data to determine the presence and number of medium-long and/or longer-duration episodes of AFib. Evaluation by the CPU can be continuous or periodic. In another embodiment, the CPU can be programmed to alert the clinician and/or patient of medium-long and/or longer-duration episodes of AFib.

In one embodiment, the patient is fitted with a wearable which can be a patch, a watch, a wristband, a strap, a ring, or any other device that adheres to the body and can operate as described above. The wearable should be engaged on the patient except for a period of temporary disengagement such as for showering, swimming, changing batteries, etc.

In one embodiment, there is provided a method to assess if a qualified patient on budiodarone therapy should be dose adjusted or disqualified which method comprises:
  a) selecting a patient qualified for and is prescribed for treatment with budiodarone by a clinician wherein said patient is fitted with a wearable wherein said wearable comprises:
    i) at least one electrode and/or optical sensor that, when the wearable is fitted, continuously or semi-continuously monitors the patient's heart rhythm;
    ii) a CPU that collects and stores the heart rhythm data; and
    iii) a transmission component that connects to the data in the CPU, wherein said transmission component is capable of initiating a communication directly or indirectly to a clinician wherein said data is optionally stored;
  c) collecting and transmitting the heart rhythm data directly or indirectly to said clinician where the data is evaluated for the presence and number of long duration episodes of AFib and the extent of AFib burden;
  d) optionally adjusting the dosing of budiodarone to access which dose is appropriate for that patient; and
  e) assessing whether the collected data evidence that the patient is or is not responsive to budiodarone therapy; wherein said therapy is maintained for responsive patients and further wherein said therapy is terminated for non-responsive patients.

In yet another embodiment, patients who are initially responsive to budiodarone therapy are continuously monitored to ensure that each of said patients remains responsive to the dose of budiodarone. If not, the clinician can adjust the dose of budiodarone or discontinue budiodarone therapy as appropriate.

In one embodiment of the above methods, the data is transmitted directly or indirectly to the clinician who can assess the presence or absence of medium-long and/or longer-duration AFib, and optionally the extent of AFib burden. The data can be stored and/or analyzed at a central analysis center, such as a "cloud" laboratory or similar site (such as a CORE laboratory), where a qualified health care professional can analyze the data and advise the attending clinician as to the patient's response and recommended adjustments to the therapy. In short, these preferred methods allow for remote patient monitoring (RPM), where the patient has no longer has responsibilities such as mailing patches for analysis and/or visiting the doctor's office.

In one embodiment, the requisite number of long duration AFib episodes and requisite extent of AFib burden to qualify for budiodarone pharmacotherapy may comprise one or more of long duration AFib episodes (e.g., at least a threshold number) of one or more minimum lengths (e.g., at least 1 hour, at least 5 hours, at least 24 hours, etc.) over a time period (e.g., over two weeks, a month, two months, etc.). As an illustrative example, the requisite number of long duration AFib episodes may comprise at least one episode of AFib lasting more than 5 hours over a month and/or at least two episodes of AFib lasting more than 1 hour over a month. A requisite extent of AFib burden may be at least a minimum extent of AFib burden (e.g., 0%—no required AFib burden, 1%, 2%, etc.). The requisite number of long duration AFib episodes and requisite extent of AFib burden may be set as is appropriate. Specific examples as part of a non-exhastive list are provided in Table 2 below:

TABLE 2

|  | # of long duration AFib episodes | AFib burden |
| --- | --- | --- |
| Embodiment 1 | At least 1 episode > 5 hours/month or at least 2 episodes > 1 hour per month | 2.5% or greater |
| Embodiment 2 | At least 1 episode > 5 hours/month or at least 2 episodes > 1 hour per month | 5% or greater |
| Embodiment 3 | At least 1 episode > 5 hours/month | 2.5% or greater |
| Embodiment 4 | At least 1 episode > 5 hours/month | 5% or greater |
| Embodiment 5 | At least 2 episodes > 1 hour per month | 2.5% or greater |
| Embodiment 6 | At least 2 episodes > 1 hour per month | 5% or greater |

In one embodiment, the wearable may comprise a storage unit for storing collected data, and the storage unit can be programmed to evaluate the stored data and alert the clinician or central analysis center of any potentially harmful heart rhythm irregularities. The collected and/or evaluated data may be continuously or periodically reviewed by the clinician or health care professional (e.g., may be pushed to a computing device accessible by the clinician continuously or periodically, and/or pulled based on a request by the computing device accessible by the clinician). Periodic evaluation can be, for example, once a day, once a week, twice a month, once a month, etc. The data collection process may be continued indefinitely, e.g., until the clinician determines that the patient's heart rhythm data either meets or fails to meet the requisite number of episodes of long duration AFib and/or the requisite extent of AFib burden. Preferably, data collection continues for at least 14 days, 30 days, 45 days, 2 months, or at least 12 weeks, or at the discretion of the attending clinician based on the history and risk factors of the patient. Patients who fail to meet established criteria for qualification are not included in budiodarone therapy.

In one embodiment, qualified patients are placed on budiodarone therapy. Such therapy includes the administration of budiodarone or a pharmaceutical composition comprising budiodarone twice a day (bid) in an amount ranging from about 200 mg bid to about 800 mg bid. The preferred dosing includes an escalating amount of budiodarone where the patient is initially dosed at 200 mg budiodarone bid. Responsive patients remain on that dose whereas non-responsive patients are dose adjusted in 200 mg increments until the patient either becomes responsive or the patient is non-responsive at all tested dose levels. In the latter case, the patient is disqualified from budiodarone therapy. In one embodiment, the qualified patients so treated are refractory to one or more other methods for treating their AFib.

The serum half-life of budiodarone is about 6 to 7 hours after administration. As a general rule, a steady state concentration of a drug is about 5× the serum half-life. In this case, the steady state would be about 30 to 35 hours. Once a steady state is achieved and allowing time for the drug to act, it is possible to initiate monitoring of a patient's heart rhythm at any point thereafter including about 3 days after initiation of therapy and preferably at least 14 days after initiation of budiodarone therapy. The latter is preferred as it allows sufficient time for the drug to be effective.

In one embodiment, the wearable is a watch, a strap, a wrist band, a ring, or a strap. In one embodiment, the watch is a smart watch.

In one embodiment, there is provided a method for reducing the risk of a patient progressing from paroxysmal AFib to persistent AFib or from persistent AFib to permanent AFib, which method comprises:
identifying a patient with either paroxysmal or persistent AFib having an AFib burden of at least 2.5% coupled with at least one episode of long duration AFib over a 4-week period;
administering budiodarone to said patient;
monitoring the efficacy of said administration and optionally adjusting the dose as needed to achieve a reduction in either or both AFib burden and long duration AFib whereupon the risk of progression from paroxysmal AFib to persistent AFib or from persistent AFib to permanent AFib is reduced; and
maintaining said monitoring to confirm the continued efficacy of budiodarone.

In one embodiment, there is provided a method for reducing the risk of heart failure in a patient diagnosed with paroxysmal AFib or persistent AFib, which method comprises:
identifying a patient with either paroxysmal or persistent AFib having an AFib burden of at least 2.5% coupled with at least one episode of long duration AFib over a 4-week period;
administering budiodarone to said patient;
monitoring the efficacy of said administration and optionally adjusting the dose as needed to achieve a reduction in either or both AFib burden and long duration AFib whereupon the risk of heart failure in said patient is reduced; and
maintaining said monitoring to confirm the continued efficacy of budiodarone.

In one embodiment, there is provided a method for reducing the risk of stroke in a patient diagnosed with paroxysmal AFib or persistent AFib, which method comprises:
identifying a patient with either paroxysmal or persistent AFib having an AFib burden of at least 2.5% coupled with at least one episode of long duration AFib over a 4-week period;
administering budiodarone to said patient;
monitoring the efficacy of said administration and optionally adjusting the dose as needed to achieve a reduction in either or both AFib burden and long duration AFib whereupon the risk of stroke in said patient is reduced;
maintaining said monitoring to confirm the continued efficacy of budiodarone.

In another embodiment, there is provided a method for reducing the risk of stroke or congestive heart failure in a patient with paroxysmal AFib or persistent AFib wherein said AFib is treated with a pharmaceutical which method comprises:
a clinician obtaining a patient's heart rhythm data from a wearable engaged by the patient wherein said wearable comprises
a) at least one electrode or optical sensor that continuously or semi-continuously monitors heart rhythm;
b) a transmission device capable of initiating transmission of data;
c) circuitry that connects the two; and
d) a CPU that collects and stores the heart rhythm data,
said clinician conducts an evaluation of said data to determine the effectiveness of the pharmaceutical by correlating the presence or absence of episodes of long duration AFib to the dose of the pharmaceutical used;
said clinician confirms that the dose of the pharmaceutical is effective or ineffective in reducing or elimination episodes of long duration AFib; and
if ineffective, said clinician increases the dose of the pharmaceutical one or more times until said dose is effective thereby reducing the risk of stroke or congestive heart failure provided that if said pharmaceutical remains ineffective when the maximum dose of said pharmaceutical is reached, said patient is removed from treatment with said pharmaceutical.

In another embodiment, there is provided a method for reducing the risk of stroke or heart failure in a patient diagnosed with AFib and treated with budiodarone which inhibits episodes of long duration AFib in said patient which method comprises:

evaluation by a clinician of the patient's heart rhythm data collected by a wearable and transmitted to said clinician from a wearable engaged by said patient wherein said wearable comprises:
- a) at least one electrode or optical sensor that continuously or semi-continuously monitors heart rhythm;
- b) a transmission device;
- c) circuitry that connects the two; and
- d) a CPU that
  - i) collects the heart rhythm data and evaluates said data for the presence of long duration episodes of AFib; and
  - ii) stores the data; and adjusting the dose of budiodarone as deemed necessary by the attending clinician in order to reduce further episodes of long duration AFib thereby reducing the risk of stroke or heart failure.

DETAILED DESCRIPTION

Figure 1:
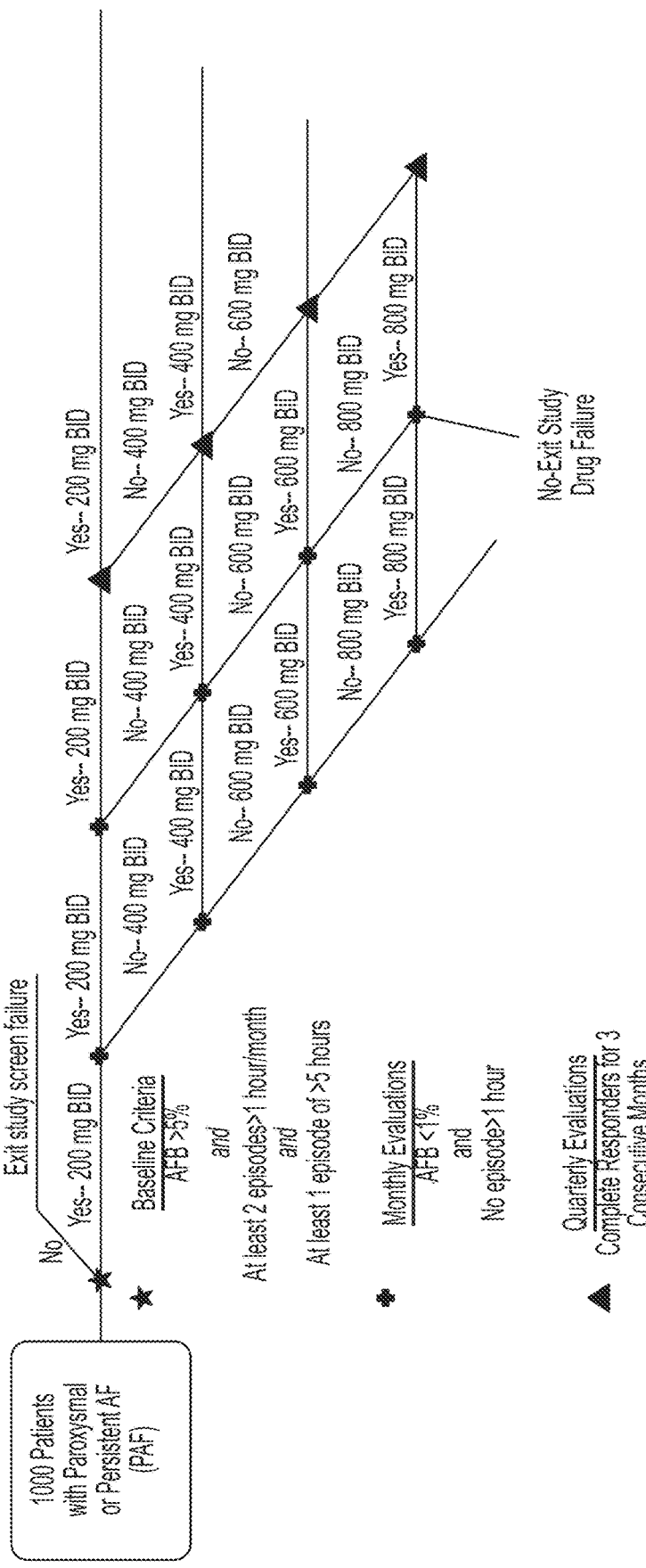
FIG. 1 illustrates a chart indicating how the patient's AFib data is used in conjunction with treatment with budiodarone.

This disclosure is directed to methods for monitoring the heart rhythm of patients diagnosed with atrial fibrillation (AFib). Such monitoring allows for modifications to the patient's treatment thereby reducing the risk of stroke and/or heart failure. However, prior to discussing the disclosure in more detail, the following terms will first be defined. Terms that are not defined are given their definition in context or are given their medically acceptable definition.

The terminology used herein is for the purpose of describing particular embodiments only and is not intended to be limiting. As used herein, the singular forms "a", "an", and "the" are intended to include the plural forms as well, unless the context clearly indicates otherwise.

Definitions

As used herein, the term "optional" or "optionally" means that the subsequently described event or circumstance may or may not occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 15%, 10%, 5%, 1%, or any subrange and/or value there between. Preferably, the term "about" when used with regard to a dose amount means that the dose may vary by +/−10%.

As used herein, the term "comprising" or "comprises" is intended to mean that the compositions or methods include the recited elements, but do not exclude others.

As used herein, the term "consisting essentially of" when used to define compositions and methods, shall mean excluding other elements of any essential significance to the combination for the stated purpose. Thus, a composition consisting essentially of the elements as defined herein, or a method consisting essentially of the steps as defined herein, would not exclude other materials that do not materially affect the basic and novel characteristic(s) of the claimed subject matter.

As used herein, the term "consisting of" shall mean excluding more than trace elements of other ingredients or substantial method steps. Embodiments defined by each of these transition terms are within the scope of this disclosure.

As used herein, the term "AFib" or "atrial fibrillation" refers to all variants of atrial fibrillation except permanent AFib. Such variants include but are not limited to paroxysmal AFib, persistent AFib, as well as paroxysmal AFib and persistent AFib with low CHA2DS2-VASc scores (2 or less) and high CHA2DS2-VASc scores (3 or higher). CHA2DS2-VASc scores stand for congestive heart failure, hypertension, age ≥75 (doubled), diabetes, stroke (doubled), vascular disease, age 65 to 74, and sex category (female) and are clinical prediction rules for estimating the risk of stroke in people with non-rheumatic atrial fibrillation (AF). A CHA2DS2-VASc score comprises a point for each of the constituent risk factors, or 2 points were indicated as (doubled).

As used herein, the term "long duration AFib" relates to a length of time an episode of AFib lasts in a patient. This length relates to the risk of stroke and/or heart failure. As is apparent, the longer the length of time a patient is in AFib, the higher the risk becomes. So, in one embodiment, a long duration AFib is any AFib episode lasting over 1 hour, provided that the AFib is not permanent. In turn, long duration AFib is further categorized by the subsets "medium-long duration" AFib, which is about 24 hours or less in duration (i.e., over 1 hour and up to 24 hours) and "longer-duration" AFib, which includes AFib episodes of over 24 hours, but which are not permanent AFib.

As used herein, the term "continuous" or "continuously" refers to monitoring conducted constantly during the engagement of a wearable by the patient. Included within the term "continuous" or "continuously" are wearables that constantly monitor the heart rhythm when worn and powered, but which may be taken off for limited periods of time (e.g., changing batteries, bathing, etc.).

As used herein, the term "semi-continuous" or "semi-continuously" refers to monitoring that is automatically done periodically by the wearable on a set schedule (e.g., every 15 seconds, every 30 seconds, every minute, and the like) without the patient's activation of the wearable. The set schedule a schedule designed to be able to monitor heart rhythm with a temporal resolution sufficient to detect AFib episodes and/or to allow determination of lengths of long duration AFib episodes.

As used herein, the terms "engageable" means that the patient can place the wearable on and off his/her body and initiate monitoring without the need for assistance from an attending health care professional. As such, engageable wearables do not include implanted (invasive) devices such as pacemakers.

As used herein, the term "monitoring the heart rhythm" means any evaluation that can be made of a patient's heart rhythm including the pulse rate, any aspect of the electric field of the patient's heart, and the like provided that such monitoring is capable of ascertaining when the patient is experiencing AFib.

As used herein, the term "initiate monitoring" includes both automatic initiation and physical initiation. "Automatic initiation" occurs when the wearable, once placed on the patient, automatically starts monitoring without any further action by the patient. "Physical initiation" means that the patient is required to activate the monitoring by physically or verbally interacting with the wearable (e.g., push a button, provide a voice command, and the like).

As used herein, the term "transmission device" means any device capable of transmitting data from the wearable. The transmission device may be included in the wearable or may be a separate device that is in communication with the wearable. The separate device can be a smart phone, a computer such as a pad, a laptop, or a desktop, and the like.

As used herein, the term "clinician" refers to a healthcare professional qualified to ascertain whether a patient's heart rhythm data correlates to sinus rhythm, atrial fibrillation, or other types of arrhythmias.

As used herein, the term "attending clinician" refers to the healthcare professional who is treating the patient with AFib. Such an attending clinician is typically a doctor or a nurse practitioner.

The term "directly" as it relates to the transmission of the patient's heart rhythm data refers to a transmission that is received by the attending clinician for evaluation regardless of whether the transmission was deposited in a Cloud site or through a number of servers, etc.

The term "indirectly" as it relates to the transmission of the patient's heart rhythm data refers to transmission to a clinician who evaluates the data and provides either the data or the conclusions reached regarding the data to the attending clinician. In such a case, the clinician can be a healthcare professional employed by a central analysis center or by the attending clinician, etc. to evaluate the heart rhythm data and provide instructions to the attending clinician either on an ongoing basis or when a change in the patient's condition warrants contact. In one embodiment, the clinician is employed by a central analysis center, a facility that reviews the data generated by its instruments and renders a diagnosis and/or recommendation that is transmitted to the attending clinician. The central analysis center has expertise in the instrument, the data generated, and the ability to analyze that data.

As used herein, a patient who is "responsive to budiodarone therapy" evidences a reduction in the number and/or duration of episodes of long duration AFib. The reduction may be a reduction by at least a certain percentage (e.g., at least 10%, preferably at least 20%, more preferably at least 30%, more preferably at least 40%, more preferably at least 50%, etc.) of one or more of the number of episodes of long duration AFib episodes and/or the duration of episodes of long duration AFib. In one embodiment, a responsive patient is a patient that evidences at least a 10% reduction in at least one of the following when measured over a 12-week period:
a) the number of long duration episodes of AFib lasting over 24 hours as compared to the number determined during qualification;
b) the number of long duration episodes of AFib lasting over 5 hours as compared to the number determined during qualification;
c) the number of long duration episodes of AFib lasting over 1 hour as compared to the number determined during qualification; or
d) a reduction in AFib burden as compared to the burden determined during qualification.

In still other embodiments, the responsive patient exhibits at least a 20% reduction, at least a 30% reduction, at least a 40% reduction, at least a 50% reduction, and/or at least a 60% reduction in one or more of a-d above over a 12 week period.

As used herein, "other methods to treat AFib" may comprise one or more blood thinners and/or other clot prevention measures, heart rate control measures, and/or heart rhythm control measures. Examples of such methods to treat AFib may include beta blockers (e.g., atenolol, bisoprolol, carvedilol, metoprolol, propranolol, timolol), Calcium channel blockers (verapamil, diltiazem), blood thinners (warfarin, coumarin, Jantoven, aspirin, apixaban, dabigatran, enoxaparin, heparin, rivaroxaban), sodium channel blockers (e.g., flecainide, propafenone, quinidine), potassium channel blockers (e.g., amiodarone, dofetilide, sotalol).

A patient may be deemed "refractory to one or more prior methods to treat their AFib" or "refractory to one or more other methods to treat their AFib" if they have been treated with the one or more prior and/or other methods to treat AFib (e.g., the other methods to treat AFib, as defined above), and their AFib has been deemed unresponsive and/or insufficiently responsive, and/or of decreasing responsiveness to the one or more methods. The "one or more prior therapies" may be ongoing and/or may have been terminated.

As used herein, the term "smart" refers to computational abilities of a device. The computational abilities of smart devices discussed herein may allow for user interaction (e.g., via a touchscreen) and/or for running applications on the smart device.

As used herein, the term "an AFib burden of at least 2.5%" means that in the absence of therapy according to the present disclosure (e.g., treatment with budiodarone and/or other heart rhythm drug), the patient has episodes of AFib where the aggregate of the duration of each episode over a set period of time is at least 2.5% of the total amount of time in said set period. So, for a patient monitored for 20 days (or 480 hours), at least 2.5% AFib burden means that the total (cumulative) period of time where the patient experiences one or more episodes of AFib is at least 12 hours (2.5% of 480 hours). This AFib burden may be independent of the number, if any, of episodes of long duration AFib. As such, the one or more episodes of AFib that in the aggregate total at least 12 hours can be a single episode or many episodes of less than 1 hour each.

As used herein, the term "budiodarone" refers to (S)-sec-butyl 2-(3-(4-(2-(diethyl amino)ethoxy)-3,5-diiodobenzoyl) benzofuran-2-yl)acetate as well as pharmaceutically acceptable salts thereof. Budiodarone is represented by the following formula:

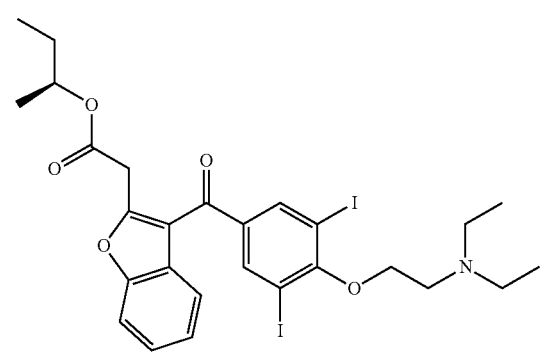 [SMILES: CC[C@H](C)OC(=O)Cc1oc2ccccc2c1C(=O)c1cc(I)c(OCCN(CC)CC)c(I)c1]

as well as pharmaceutically acceptable salts thereof.

The term "wearable" refers to any device that can be worn by a user, e.g., as an accessory, as clothing and/or embedded in clothing, etc. In an embodiment, a wearable device herein may be capable of measuring the heart rhythm of a user thereof without implantation (such as surgical and/or subcutaneous implants).

As used herein, a patient is "fitted with a wearable" when the wearable is being worn by, or is otherwise fixed to, the patient so as to be able to measure the heart rhythm of the patient.

As used herein, the term "baseline" refers to a patient who has AFib and is monitored to determine the extent of AFib burden and the number of episodes of long duration AFib over a set period of time prior to treatment with budiodarone. In such a case, measuring the baseline prior to therapy over a set period of time provides for the current state of the disease. In most if not all cases, the baseline state of the disease is unknown to the attending clinician and is necessary information to determine if subsequent treatment with budiodarone is effective.

Instrumentation

The instrumentation used in the methods described herein may be used for pharmacotherapy as described herein, as opposed to merely for diagnosis. Using wearables merely for diagnosis is conventional and aims to inform the clinician whether the patient either has AFib or not and/or, if the patient has AFib, possibly information about the patient's AFib burden and the number of episodes of AFib. Such diagnostic analysis fails to address any pharmacotherapeutic suitability, efficacy, and/or dose, which extend beyond diagnosis. The pharmacotherapeutic methods described herein include identifying patients who qualify for drug therapy and/or monitoring the qualified patient during treatment with the pharmacotherapy to assess the drug's effectiveness (e.g., in reducing the number of episodes of long duration AFib). The monitoring may allow for dose adjusting for the patient until the patient is deemed to be responsive to therapy or is disqualified from pharmacotherapy due to a failure to respond. The pharmacotherapeutic methods described herein may provide for limited (e.g., one or more periods of a discrete period, such as a period of about two or four or six weeks) and/or indefinite (e.g., without a preset end-date) monitoring of the patient to establish qualification for drug intervention and/or to ensure that the patient is and/or remains responsive. Accordingly, the wearables described herein are designed and/or selected to be robust for extended use, and/or comfortable and/or easy to use by the patient.

In practice, the wearable may include a cardiac monitoring component, which may be either an assisted or an unassisted component, for measuring heart rhythm in patients. The wearable may be engageable and disengageable by the patient and do not involve invasive procedures common to non-wearables, such as pacemakers, implantable cardioverter defibrillators (ICD), and the like. The specific cardiac monitoring component employed in the wearable is not critical, provided it can accurately measure the heart rhythm. The wearable may be capable of reporting measured heart rhythm data, such as by generating and/or transmitting data indicating a length of time of a detected period of AFib, and/or by generating and/or transmitting data indicating a number of episodes of long duration AFib detected (e.g., over a time period of interest, such as a week, a month, etc.). Also, or alternatively, the wearable may be configured to transmit heart rhythm data to a device configured to detect AFib and/or determine a length of time of a detected period of AFib and/or a number of episodes of long duration AFib (e.g., over the time period of interest). The wearable is approved by one or more regulatory bodies, such as the US Food & Drug Administration (FDA).

Assisted Components

An assisted cardiac monitoring component may use photoplethysmography (PPG) to detect heart rate and rhythm. PPG is a conventional technology found in standard oximeters, measures light reflection in tissue to detect arterial pulsations and, accordingly, heart rhythm patterns. However, to continuously and/or semi-continuously measure heart rhythm, one must account for the fact that PPG signals generated during patient movement are often distorted, weak and noisy. To account for such deficiencies, an algorithm may be used to reduce enough of the distortion and/or noise to provide for a reliable signal. In one embodiment, both a PPG sensor and accelerometer are employed with an algorithm that allows for appropriate (e.g., sufficient signal to noise ratio). When so assisted, PPG may allow for a reliable detection of both heart rates and heart rhythm. See, for example, Wojcikowski, et al., *Photoplethysmographic time-domain heart rate measurement algorithm for resource-constrained wearable devices and its implementation*, Sensors 20, no. 6 (2020): 1783 which is incorporated herein by reference in its entirety.

In some embodiments, the cardiac monitor component uses piezoelectric material and/or rhythm electroactive polymers to detect blood flow, thereby indirectly measuring heart rhythm.

In some embodiments, a combination of PPG and/or piezoelectric measurements and electrocardiogram data from single-electrode wearables (iECG, as opposed to ECG, which will refer to a conventional multiple-electrode electrocardiogram) can be combined in order to increase the specificity of the measurement. The iECG and the PPG or the piezoelectric data can originate either from two separate devices communicating by transceivers, for example, an armband and a smartwatch, or they can originate from a single device, for example, a wrist band on a smartwatch (for example, the Kardia Band on an iWatch). Once an arrhythmia is detected in the PPG data, the corresponding (e.g., in time) iECG data may be analyzed by an algorithm.

Unassisted Components

In another embodiment, the wearable may include an unassisted cardiac monitor component, such as a portable electrocardiogram. The portable electrocardiogram component may be wearable, engageable at will by the patient, and/or capable of transmitting data, e.g., via a built-in antenna. The wearable comprising the unassisted cardiac monitor component is able to measure heart rates and heart rhythms. The wearable may be configured to detect and log AFib burden and/or long duration (episode) of AFib (LEAF) over an observation period (e.g., of about 2 weeks or longer). The unassisted cardia monitor component employs direct measurement, which means that the device is reading electrical signals generated by the heart. The direct measurement may be less affected by noise and distortion than indirect measurements, such as PPG measurements, which may enable transmitting measurement data to a clinician without the use of an algorithm, and/or with reduced use of any algorithm or data processing.

In some embodiments, the wearable may include a specialized accessory, such as a cardiac monitor device, that can detect the electrical activities of a heart including heart rhythm through an electrode. The specialized accessory may be capable of initiating transmission and/or may comprise and/or be connected to a transmission device.

In some embodiments, the cardiac monitor device can be a component that is an integral part of a single wearable device, such as a smart watch. By providing a single device that is wearable by a user and is capable of monitoring the electric field of the heart of the user, the electrical activities of the heart can be monitored continuously over a prolonged period, such as days or even months.

In some embodiments, the cardiac monitor device may include an analog-to-digital convertor capable of digitizing measured electric field data (e.g., measured potential difference data) so as to transmit and/or stored in memory the measured data as digitized data. The cardiac monitor device can include an output that can transmit signals carrying information about the difference of potential between the limb and the body to an external circuit. The output can take various forms. In one case, the output can be a transceiver that communicates to another transceiver/receiver in another unit, for example, a watch or a tablet. In one embodiment a central analysis center (e.g., a remote lab, such as a CORE lab and/or a remote data analysis center and/or a server) may interpret and/or summarize the AFib data and/or the LEAF data. The central analysis center may also transmit a dose adjustment recommendation to the treating clinician, without a need for the patient to visit his or her physician (e.g., as part of a patient monitoring program). Also, or alternatively, an artificial intelligence algorithm may be used to determine the dose adjustment, and may transmit the dose adjustment recommendation to the physician.

Further Aspects

In one embodiment, the wearable may be a small consumer electronic device, for example, a watch, an armband, a ring, a strap, and/or a wrist band. The wearable may include a housing that carries the cardiac monitor component and any associated circuitry, CPU, and the like. The wearable can also be worn at other locations on the user, including, but not limited to, the wrist, leg, neck, and/or body. The wearable may comprise a specialized accessory capable of communicating with another electronic device such as a tablet, a laptop computer, a desktop computer, and/or other similar devices, which, in turn, can communicate to a cloud network to transmitted information from the device to the clinician. Also, or alternatively, the specialized accessory may be capable of transmitting information directly and/or via a network to the clinician.

The heart rhythm and iECG wearables may be Bluetooth, Z-Wave, Zigbee, and/or Advanced and Adaptive Network Technology (ANT)-enabled. For example, the iECG and/or the heart rhythm monitoring and/or recording device (e.g., a PPG or piezoelectric heart rhythm monitoring and/or recording device) may be paired with an application that may be configured to automatically detect AFib based on data from the iECG and/or the heart rhythm monitoring and/or recording device. The iECG device and/or the rhythm monitoring and/or recording device may be configured to transmit data to the application. The data may be transmitted using one or more of Bluetooth, Z-Wave, Zigbee, or ANT protocols. The application may be configured to analyze the data using a proprietary software. Based on the data from the iECG and/or the heart rhythm monitoring and/or recording device, the application may be able to interpret and/or detect AFib with a sensitivity >90% and a specificity >80%.

Patients with a wearable as described herein can use the wearable to record heart rhythm and detect AFib. The recording can be continuous and/or semi-continuous. The specifics of the recording can be programmed into the device, directly or indirectly (e.g., remotely). AFib data may be stored securely, such as in a cloud-based data repository using highly secured protocols.

Examples of commercially available assisted and unassisted wearables include, without limitation, the following:

MCOT® wearables sold by Philips Biosciences. Best, Netherlands. This device is a wearable patch that can send iECG data automatically via a wireless connection to a central analysis center (e.g., a CORE lab). This system is configured to provide data sufficient to enable a clinician to determine if dose escalation and/or drug discontinuation is warranted.

An ePatch extended wear Holter monitoring system sold by Philips Biosciences. Best, Netherlands. This device is configured to record data indicating AFib and/or long duration (episode) of AFib (LEAF). This device is configured to record and/or store iECG data continuously. This data is then archived and analyzed centrally.

There are a number of other wearables, some of which are FDA approved, which can be used in placed of those recited above including, by way of example only, Zio by iRhythmtech, San Francisco, California, USA; Frontier X2, Fourth Frontier, Austin, Texas, USA, wearables by VivaLink, Campbell, California, USA, just to name a few. The above and other wearables discussed herein represent a non-exhaustive list of wearables suitable for use in the methods described herein. The specific wearable to be used is not critical, as long as it is capable of measuring heart rhythm (e.g., generating a signal and/or data from which heart rhythm can be determined). The wearable used should be capable of measuring the heart rhythm of a patient fitted with the wearable continuously or semi-continuously for a required time period as described herein (e.g. a required time period for determining a baseline, for monitoring during pharmacotherapy, etc.). Further, the wearable should be small enough and/or comfortable enough for a patient to wear and/or be fitted with the wearable for the required time period.

Methodology

The disclosed methods allow the attending clinician to identify and/or treat a qualified patient with pharmacotherapy, as well as to assess the efficacy of the therapy based on heart rhythm data monitored over a period of time. The period of time may be an extended period of time, which may be measured in weeks, months, and/or years. The monitoring may comprise monitoring heart rhythm data and/or using said heart rhythm data to determine a condition of the patient's AFib, which may be determined based on one or more of the patient's AFib burden or the number or duration of AFib episodes over the period of time (e.g., a frequency of AFib episodes and/or long duration AFib episodes). This represents a new paradigm in treating AFib, as it allows the clinician to do one or more of the following:

assess the extent of the disease in the patient;
determine if the patient qualifies for pharmacotherapy;
evaluate the efficacy of the therapy, in the short term (1-6 months) and/or in the long term (after 6 months);
dose adjust the patient to achieve and/or maintain a therapeutic result; and/or
remove patients from pharmacotherapy if they are non-responsive to the therapy.

In contrast thereto, conventional monitoring of a patient is typically diagnostic in nature, e.g., conducted during a single short-duration period typically of no more than two-weeks using a Holter monitor or the equivalent. Such diagnostic methods allow the clinician to at best confirm the presence of AFib. In most cases, the clinician will then place the patient on blood thinners. Alternatively, the clinician can place a diagnosed patient on pharmacotherapy, which might involve heart rate reduction using beta-blockers and/or calcium channel blockers. Regardless, once diagnosed, conventional monitoring is typically terminated.

In cases where a clinical evaluation of AFib is done for clinical investigative purposes, it is common to use an implantable (invasive) device that requires surgical insertion and, subsequently, surgical removal. Such investigations are typically done in order to understand the underlying risks of stroke and congestive heart failure are relative to either the AFib burden and/or AFib duration. See, for example, Turakhia M. P. et al., Circ Arrhythm Electrophysiol., 2015, 8(5):1040-7 and many others. In some cases, non-invasive means to monitor the patients were sometimes used but typically the monitoring is of short duration. See, e.g., Go, et al., JAMA Cardiology, 2018, 3(7):601-608. Regardless, such clinical evaluations failed to address methods for delivering budiodarone to a patient and then evaluating the effect of this drug on the patient's AFib burden or episodes of long duration AFib over extended periods of time with the option to dose adjust patients to achieve the desired therapeutic result.

Unlike prior protocols for treating AFib using drugs that limited the patient's heart rate, the methods described herein are directed to treating the patient's heart rhythm in order to reduce the causative reasons for stroke and heart failure. By coupling the ability to continuously or semi-continuously monitor the heart rhythm with suitable drugs that limit the number and extent of long duration episodes of AFib, the clinician can significantly reduce the risk of stroke or congestive heart failure. Still further, by monitoring the patient after initiation of drug therapy, the clinician can now evaluate the efficacy of the drug, adjust the dose as needed to enhance overall efficacy or to identify those patients who are non-responders to such therapy who are removed from the therapy.

One embodiment of this approach is depicted in FIG. 1, which schematizes an iterative process to evaluate a patient, qualify a patient for budiodarone therapy, and treat the qualified patient. In FIG. 1, an exemplary cohort of patients, who have been diagnosed with either paroxysmal and/or persistent AFib, are evaluated for their AFib burden. Those evidencing a suitable AFib burden ("Yes" at star decision point), in this case, 5% or more, but this AFib burden may be a different threshold, such as 2.5%, and/or a patient and/or cohort specific threshold, may be selected to continue in the qualification process, while those who fail to meet this threshold are excluded ("No" at star decision point). The patients may also be evaluated for the duration of their AFib episodes. In this particular embodiment, patients are further qualified for budiodarone therapy ("Yes" at star decision point) if there is evidence of at least 1 episode of AFib lasting more than 5 hours over a 1-month period and/or two or more episodes of AFib lasting more than 1 hour over a 1-month period. Patients who fail to meet either of these criteria are excluded ("No" at star decision point) as presumably having a very low risk of stroke or congestive heart failure. Qualified patients are placed on an ascending dose regimen of budiodarone, which has been shown to significantly reduce episodes of AFib, including episodes of long duration AFib, which, by definition, reduce AFib burden. Other drugs that behave similarly to budiodarone may be used in place of and/or in addition to budiodarone in the methods described herein.

In the iterative process of FIG. 1, an ascending regimen is employed to assess whether budiodarone is effective in treating long duration episodes of AFib and/or at what dose(s). Given that the AFib burden and/or the number and duration of episodes of long duration AFib vary from patient to patient, different doses of budiodarone may be effective for different patients. However, heretofore, a clinician prescribing budiodarone at a first dose was blinded from whether that dose was efficacious. As per FIG. 1 and the Examples below, the methods described herein allow the clinician to assess efficacy at a first dose and/or to dose adjust in an ascending and/or descending protocol in an iterative process until either a therapeutic result is achieved, and/or the patient is deemed to be a non-responder. As to such non-responders, they are removed from budiodarone therapy.

In an ascending regimen, patients are first administered a low dose and may have the dose increased in case the patient is non-responsive and/or insufficiently responsive (e.g., "No" at the plus signs). A patient may be determined non-responsive if they do not respond to a maximum dosage. A descending regimen can also, or alternatively, be employed, in which a highest dose of budiodarone is administered to the patient and efficacy is determined for decreasing dosages. One advantage of a descending protocol is that non-responders could be determined in the first iteration and not the last. However, an ascending protocol may have benefits of first finding a lowest effective dosage and/or reducing the risk of side-effects.

In one embodiment, treatment of a patient with budiodarone may result in reducing a number and/or frequency of episodes of long duration AFib and/or may result in reducing the AFib burden. This is in contrast to drugs that reduce heart rate but have little to no ability to reduce the duration AFib episodes and/or the AFib burden. AFib burden and episodes of long duration AFib are distinct. As to AFib burden, the number and duration of each AFib episode in a patient is measured to determine an AFib burden. A patient with a enough of only very short duration episodes of AFib may still be assigned a higher AFib burden than a patient with infrequent episodes of long duration AFib. Hence, a patient who has 8 episodes of AFib each having a duration of 45 minutes in a given 24-hour period would be assigned a AFib burden of 25% (6 hours/24 hours). In contrast thereto, a patient with a single episode of AFib lasting for 5 hours during a 24-hour period would be assigned an AFib burden of 20.8%. However, the latter patient with the single AFib episode may be at greater risk of a stroke than the former patient. Accordingly, patients having an AFib burden of less than 2.5% are very unlikely to have long duration AFib and, accordingly, may be determined not qualified for treatment with budiodarone.

Still further, transitioning a patient from either paroxysmal AFib to persistent AFib or from persistent AFib to permanent AFib may be undesirable as it may evidence unwanted disease progression. Because budiodarone reduces the extent of long duration AFib and the number of AFib episodes, the combination of these reductions inhibits the progression of the disease and, in some cases, may revert such a transition.

In comparison, treatment of AFib with blood thinners does not address the cause of AFib, does not reduce the underlying concerns with either AFib burden and/or with episodes of medium duration and longer-duration AFib. Moreover, using blood thinners does not prevent a patient from progressing from paroxysmal AFib to persistent AFib or from persistent AFib to permanent AFib. Still further, the use of blood thinners introduces another set of issues with bleeding, such as bleeding that leads to death.

In view of the above, according to the present disclosure, a patient's heart rhythm may be monitored over an extended period to assess the efficacy of a drug that is intended to control such long duration episodes. Devices such as a Holter monitor can be used to monitor a patient's heart rhythm over a short period of time (e.g., 1 day, 2 days, or 3 days and even up 14 days), but such monitoring cannot provide a comprehensive and ongoing analysis of the patient's AFib and/or how a drug treatment is impacting the number and duration of episodes of AFib over extended periods of time (e.g., of weeks or more). Such short-duration analysis provides only a diagnostic analysis, not a therapeutic analysis, and fails to provide a full picture of the heart health of the patient. Due to the erratic and dynamic nature of AFib, and variability across patients, an accurate measurement of AFib in a patient can only be obtained by monitoring over prolonged periods of time, such as longer than 1 month, longer than 3 months, etc.

Drug Therapy

There are many conditions where the attending clinician can evaluate a patient based on a static number that represents a meaningful long-term average. For example, in diabetes, the three-month value for hemoglobin AIC (also referred to as HbA1C test is a blood test) provides an excellent indicium for the average daily blood glucose levels. In addition, liver function, prostate health, thyroid health, etc. can all be evaluated based on a specific number that provides meaningful information to the clinician.

The clinicians treating paroxysmal and/or persistent AFib have had to rely upon brief monitoring of the patient's heart rhythm, such as an ECG (electrocardiogram) and/or a Holter monitor. However, such brief monitoring may miss critical data points that could only be obtained by monitoring over longer periods of time. This may cause a clinician to avoid pharmacotherapy without a means to monitor the drug's effectiveness in the patient. Rather, a patient diagnosed with AFib may be placed on symptom and/or risk reduction treatments, such as blood thinners. However, while blood thinners will reduce the risk of clot-related strokes (e.g., clots arising from AFib), there is a corresponding increased risk of uncontrolled bleeding which can lead to death.

Pharmaceuticals, such as sotalol, as well as beta-blockers and calcium channel blockers, have been used to treat AFib. Examples of calcium channel blockers include amlodipine, diltiazem, felodipine, isradipine, nicardipine, nifedipine, nisoldipine, and verapamil. Examples of beta blockers include acebutolol, atenolol, bisoprolol, metoprolol, nadolol, nebivolol, and propranolol. Drugs with combined modes of action, such as amiodarone, also exist. Budiodarone, a drug with a combined mode of action, has been shown to reduce episodes of long duration AFib without a significant increase in the QT interval. Indeed, budiodarone represents a significant advancement in treatment for AFib, since episodes of long duration AFib are substantially the cause of clot formation that may lead to strokes and/or congestive heart failure. However, AFib is a variable disease, with some patients requiring different dosing of a drug to achieve desired results. As noted earlier, the inability to monitor patients in a manner that could evaluate the effectiveness of the drug was a major drawback to pharmaceutical intervention. This has led to clinicians opting for the use of blood thinners and/or risk reduction measures, instead of proactive pharmaceutical intervention.

The wearables and methods described herein provide sufficient data to the clinician on an ongoing basis to determine the long-term effectiveness of drugs in treating paroxysmal and persistent AFib. As such, methods that integrate data generated by wearables with a drug that can control long duration AFib and/or reduce AFib burden may allow for more effective treatment of AFib, which is a long felt need in the art. Moreover, the ability to determine the long-term effectiveness of a drug may allow for dose-adjusting the patient to effectively achieve control over episodes of long duration of AFib.

Treatment Regimens Using Budiodarone

Budiodarone has been shown to reduce episodes of long duration AFib in patients thereby reducing the risk of stroke and congestive heart failure. However, to effect therapy over a broad spectrum of patients having varying frequencies in the number and duration of episodes of long duration of AFib using budiodarone requires that the clinician monitor each patient for efficacy at a given dose. Such represents a personalized medicine approach to a disease that is treatable by budiodarone.

If a patient is non-responsive at that dose, an increase in dosing is warranted and the process is repeated until it is determined that the patient is responsive at a given higher dose or is non-responsive. Patients who are non-responsive at all tested doses are removed from budiodarone therapy.

Still further, patients who have either paroxysmal or persistent AFib and, who are refractory to one or more prior methods for treating their disease, may be candidates for the methods and procedures described herein. Such patients may be screened (qualified) for treatment by determining their baseline AFib burden and/or the number and extent of their long duration AFib episodes. Their baseline may also be used to assess the relative reduction in and/or the complete elimination of these symptoms based on budiodarone therapy and/or to identify patients as non-responders to budiodarone therapy. Accordingly, a method to treat patients with paroxysmal or persistent AFib, wherein said patients are refractory to one or more prior therapies to treat their AFib, may comprise:

a) selecting a patient who is refractory to the one or more prior methods to treat AFib;
 b) identifying the number of episodes of long duration AFib and the extent of their AFib burden, wherein the identified number and extent satisfy criteria to qualify the patient for treatment with budiodarone by a clinician;
 c) fitting said patient with a wearable, wherein said wearable comprises:
  i) at least one electrode and/or optical sensor that, when the wearable is fitted, continuously or semi-continuously monitors the patient's heart rhythm;
  ii) a CPU that collects and stores the heart rhythm data; and
  iii) a transmission component configured to access the data in the CPU, wherein said transmission component is capable of initiating a communication directly or indirectly to a clinician;
 d) causing collecting and transmitting of the heart rhythm data directly or indirectly to a clinician, where the data is evaluated for the presence and number of long duration episodes of AFib and the extent of AFib burden;
 d) optionally adjusting the dosing of budiodarone to determine an appropriate dose for the patient; and
 e) assessing whether the collected data evidence that the patient is or is not responsive to budiodarone therapy; wherein said therapy is maintained for responsive patients and further wherein said therapy is terminated for non-responsive patients.

Because of the lack of sufficient information to ascertain the efficacy for a given dose of any drug prescribed to reduce the number of episodes of long duration AFib in the treated patient, a clinician would invariably avoid doing so particularly given the variability in patients as well as in the disease itself. Still further, many clinicians view that treating (reducing) the heart rate as an appropriate method for treating AFib optionally coupled with blood thinners. See, for example, Atrial Fibrillation—Treatment, https://www.nhs.uk/conditions/atrial-fibrillation/treatment/where, in 2021, the authors were controlling heart rates as part of an appropriate approach to treating AFib. Taken together, the use of a wearable that could generate data as to a patient's response to a given dose of budiodarone over an extended period of time was not contemplated. Now, as per the methods described herein, a clinician can evaluate a patient's heart rhythm data over at least 2 weeks, over at least 1 month, over at least 3 months, and/or over at least 6 months and potentially for the remainder of the patient's life, so as to determine the number and/or duration of episodes of long duration AFib; based on that determination assess whether the patient should be placed on budiodarone therapy; and, if so, assess the patient's response to varying doses of budiodarone.

In one embodiment, which is illustrated in the Examples and FIG. 1, for example, the clinician may initiate dosing of budiodarone at a minimal level of about 200 mg twice a day (bid) and then assess whether that dose is effective in eliminating episodes of long duration AFib. The clinician can review data at the initial dosing level and dose-adjust one or more times, e.g., as necessary to arrive at a dose where the patient is substantially free of and/or is free of episodes of long duration AFib. In general, the incremental increases in dosing can be about 200 mg twice a day. So, in this approach, the dosing can be changed from about 200 mg bid, to about 400 mg bid, or to about 600 mg bid, and so on up to about 800 mg bid and possibly higher if the attending clinician determines that there is a benefit to higher doses.

Systems

The methods described herein can be conducted either in a unitary device, such as a wearable that has the ability to record, store and transmit the heart rhythm data. However, systems of multiple devices can also be used, provided that such systems include:

a) a wearable that collects heart rhythm data from a patient diagnosed with either paroxysmal atrial fibrillation and/or persistent atrial fibrillation;
b) a CPU that is in communication with the wearable that collects and stores the data; and
c) a transmission device that communicates with the CPU and that sends the data directly and/or indirectly to one or more designated recipients.

EXAMPLES

In the examples that follow, and in the specification, the following abbreviations have the following meanings. If an abbreviation is undefined, then it has its conventional medical meaning.

AFib or AF=atrial fibrillation
bid=twice a day
bpm=beats per minute
hrs=hours
mg=milligrams
PPG=photoplethysmography
SD=standard deviation Example 1 is provided to illustrate that the use of a wearable can detect AFib episodes during continuous monitoring of a patient.

Examples 2-7 establish the utility of budiodarone in the methods described herein. In these examples, the patients all had surgically implanted pacemakers and as such carried a number of risks associated therewith. See, e.g., Pacemaker, https://www.mayoclinic.org/tests-procedures/pacemaker/about/pac-20384689, (last visited Oct. 26, 2022) which is incorporated herein by reference in its entirety.

Example 1—Wearables that Detect AFib in Patients on a Continuous Basis

In this example, a male patient suffering from non-permanent AFib was fitted with a MCOT wearable device sold by Philips BioSciences, Inc., Best, The Netherlands and commercially available by prescription in the United States. The MCOT device employs PPG coupled with an algorithm to assess heart rhythm and AFib. The MCOT device is configured to wirelessly and seamlessly provide heart rhythm and AFib data to a dedicated computer.

Figure 2:
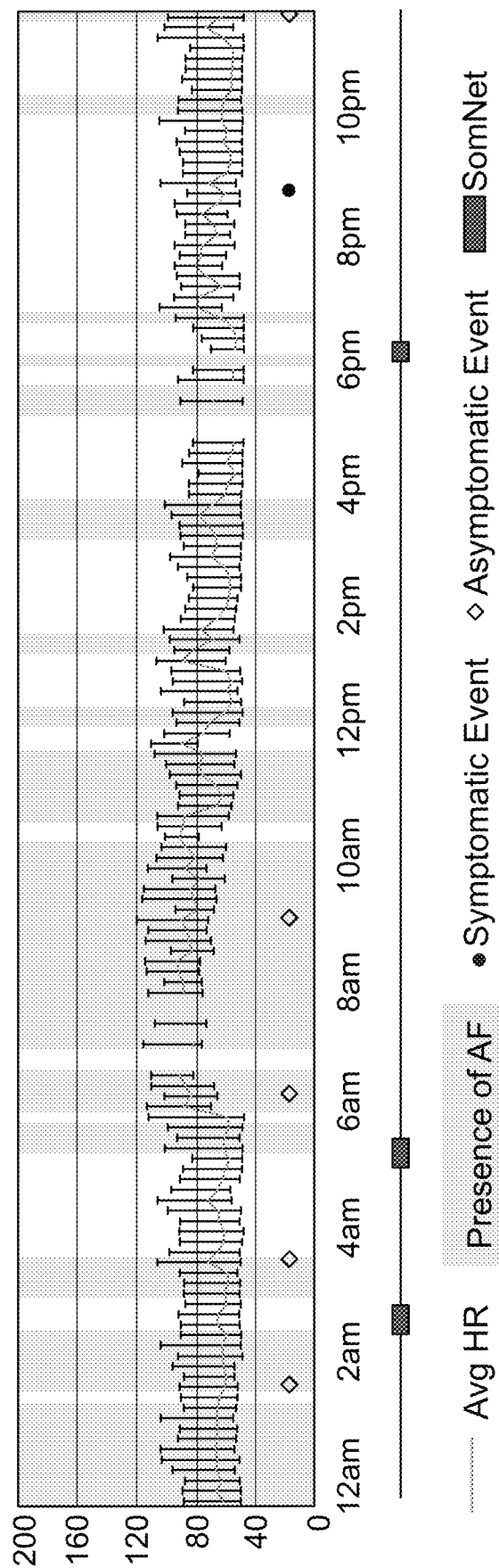
FIG. 2 illustrates a cardiogram of a patient with intermittent AFib.

The patient was continuously monitored over a period of 23.5 hrs. During the entire period, the MCOT device measured the patient's heart rhythm and rate. FIG. 2 provides a cardiogram obtained during the monitoring period. Of note is that there were 33 separate episodes of AFib detected and recorded each separated by periods of sinus rhythm or other arrhythmias. The specific details of the analysis of the cardiogram are as follows:

| | |
|---|---|
| Number of AFib Episodes | 33 |
| Longest Period in AFib | 3 hours and 2 minutes |
| Heart Rate (minimum/maximum) | 48/94 beats per minute |
| AFib Burden | 36% |

The above data demonstrates that a wearable as described herein was capable of continuously monitoring the patient heart rhythm and provided detailed analysis of the number of AFib episodes as well as the extent of AFib burden.

Example 2—Elimination of Long Duration AFib with Budiodarone

This example is a clinical trial evaluation of budiodarone in treating 6 patients with paroxysmal or persistent AFib who previously evidenced episodes of long duration AFib (greater than 24 hours). In this example, the patients' heart rhythm was continuously monitored over a two-week period with a pacemaker, and were treated with different doses of budiodarone. The purpose of this example is to establish whether budiodarone reduces long duration AFib lasting more than 24 hours. The different doses and results of this evaluation are provided in Table 3 below:

TABLE 3

| Parameter Mean (SD) | Baseline | 200 mg Bid | 400 mg bid | 600 mg bid | 800 mg bid | Washout |
|---|---|---|---|---|---|---|
| # of AFib episodes | 22 (22) | 31 (28) | 37 (54) | 42 (66) | 24 (28) | 37 (49) |
| Duration of episodes | 4.8 (5.2) | 1.7 (2.5) | 0.6 (0.7) | 0.1 (0.2) | 0.5 (0.7) | 2.5 (5.0) |
| Duration of sinus rhythm | 23 (21) | 131 (162) | 48 (57) | 103 (148) | 42 (70) | 40 (43) |
| Longest AFib Episode - hrs | 50 | 7 | 13 | 7 | 5 | 105 |

The above results demonstrate that budiodarone eliminated over 70% of the episodes of long duration AFib lasting more than 24 hours as compared to Baseline for all dose levels with little differences between treatment levels of 200 mg bid, 600 mg bid and 800 mg bid. In contrast, both baseline and washout results evidence the presence of episodes of long duration AFib lasting more than 24 hours. These results also evidence a significant reduction (more than 64% reduction) in AFib burden (the number of episodes over a 2-week period times the average duration of the episodes). This reduction correlates well with reducing the risk of a patient transitioning from paroxysmal AFib to persistent AFib or from persistent AFib to permanent AFib.

Example 3—Elimination of Longer Duration AFib (>24 Hours) During a 12-Week Period This example is a clinical trial evaluation of budiodarone in treating 6 patients with either paroxysmal or persistent AFib who previously evidenced episodes of long duration AFib (greater than 24 hrs). In this example, the patients' heart rhythms were continuously monitored over a twelve-week period with a pacemaker (surgically invasive procedure) and were treated with different doses (2 weeks each) of budiodarone. In addition, during this trial, the patients were under continuous monitoring and constant clinician supervision.

The purpose of this example is to establish whether budiodarone treatment can reduce longer duration AFib (AFib episodes lasting more than 24 hours) in a clinical study setting and using a pacemaker to evaluate heart rhythm. The results of this analysis are provided in Table 4 below:

TABLE 4

| Episodes of AFib > 24 hrs | Number | Duration |
|---|---|---|
| Off Drug (baseline) | 4 | 219 (100%) |
| 200 mg bid | 0 | 0 (0%) |
| 400 mg bid | 0 | 0 (0%) |
| 600 mg bid | 0 | 0 (0%) |
| 800 mg bid | 0 | 0 (0%) |

"Number" indicates the number of longer duration episodes of AFib (i.e., having a duration of greater than 24 hours). "Duration" indicates the amount of time during the 2-week period spent in the longer duration indicated in hours and a percentage relative to the baseline measurement. As per the above results, 200 mg b.i.d. was sufficient to treat all patients in the study by eliminating the number of episodes of AFib lasting over 24 hours. In this case, dose escalation was not required to improve patient efficacy as the 200 mg bid doses of budiodarone were sufficient to eliminate these long duration episodes of AFib.

Example 4—Reduction of Long Duration AFib (>5 Hours) During a 12-Week Period

This example is a clinical trial evaluation of budiodarone in treating 6 patients with either paroxysmal or persistent AFib who previously evidenced episodes of long duration AFib (greater than 5 hrs). In this example, the patients' heart rhythms were continuously monitored over a twelve-week period with a pacemaker (surgically invasive procedure) and were treated with different doses (2 weeks each) of budiodarone. In addition, during this trial, the patients were under continuous monitoring and constant clinician supervision.

The purpose of this example is to establish whether budiodarone reduces long duration AFib lasting more than 5 hours in a clinical study setting using a pacemaker to evaluate the heart rhythm. The results of this analysis are provided in Table 5 below:

TABLE 5

| Episodes of AFib > 5 hrs | Number | Duration |
|---|---|---|
| Off Drug (baseline) | 29 | 490 (100%) |
| 200 mg bid | 3 | 17 (3.5%) |
| 400 mg bid | 4 | 38 (7.7%) |
| 600 mg bid | 2 | 14 (2.8%) |
| 800 mg bid | 1 | 5 (1%) |

"Number" indicates the number of long duration episodes of AFib having a duration of greater than 5 hours. "Duration" indicates the amount of time during the 2 week period spent in the greater than 5 hour duration AFib, indicated in hours and a percentage relative to the baseline measurement. In this example, all doses of budiodarone provided significant benefits in reducing both the number and duration of AFib episodes over 5 hours, with both the 200 mg bid and the 600 mg bid providing similar results whereas the results for 400 mg bid were exceptionally better than Off Drug condition, but inferior to the 200 mg bid and the 600 mg bid. Finally, the 800 mg bid performed best. In all doses, the reduction in episodes of AFib of greater than 5 hours were above 85% and the corresponding reduction in AFib burden was above 90%.

In light of the previously discussed relation between long duration AFib episodes and increase the risk of stroke and heart failure (see, e.g., Singer, et al., Temporal Association Between Episodes of Atrial Fibrillation and Risk of Ischemic Stroke, JAMA Cardiology, 6(12):1364-1369 (2021)), the next comparative example measured the reduction in AFib episodes of 1 hour or more.

Example 5—Reduction of Long Duration AFib (>1 Hours) During a 12-Week Period

This example is a clinical trial evaluation of budiodarone in treating 6 patients with either paroxysmal or persistent AFib who previously evidenced episodes of long duration AFib (greater than 1 hour). In this example, the patients' heart rhythms were continuously monitored over a twelve-week period with a pacemaker (surgically invasive procedure) and were treated with different doses (2 weeks each) of budiodarone. In addition, during this trial, the patients were under continuous monitoring and constant clinician supervision.

The purpose of this example is to establish whether budiodarone reduces long duration AFib (duration >1 hr) in a clinical study setting using a pacemaker to evaluate the heart rhythm. The results of this analysis are provided in Table 6 below:

TABLE 6

| Episodes of AFib > 1 hrs | Number | Duration |
|---|---|---|
| Off Drug (baseline) | 66 | 598 (100%) |
| 200 mg bid | 22 | 60 (10%) |
| 400 mg bid | 12 | 56 (9.3%) |
| 600 mg bid | 6 | 26 (4.3%) |
| 800 mg bid | 6 | 15 (2.5%) |

This example demonstrates a substantial reduction in the number of episodes of long duration AFib (>1 hrs) over a 2 week period. As above, "Number" indicates a number of long duration AFib episodes during the 2 week period, and "Duration" indicates a number of hours during the 2 week period sent in the long duration AFib episodes Example 6—Reduction in Episodes of AFib Greater than 6 Minutes During a Twelve Week Period This example shows the robust nature of budiodarone in reducing both AFib burden and episodes of AFib greater than 6 minutes (0.1 hour) in 6 patients with either paroxysmal or persistent AFib and who previously evidenced episodes of long duration AFib (greater than 1 hr). In this example, the patients' heart rhythm was continuously monitored over a twelve-week period with a pacemaker. The patients were treated with different doses (2 weeks each) of budiodarone. In addition, during this trial, the patients were under continuous monitoring and clinician supervision.

The results of this example are summarized in Table 7 and establish that budiodarone not only reduces long duration AFib lasting more than 1 hour in a clinical study setting using a pacemaker to evaluate the heart rhythms, but also significantly lowers episodes of greater than 6 minutes (0.1 hours).

TABLE 7

| Episodes of AFib > 0.1 hrs | Number | Duration in hours |
|---|---|---|
| Off Drug (baseline) | 99 (100%) | 616 (100%) |
| 200 mg bid | 52 (52%) | 71 (11%) |
| 400 mg bid | 28 (28%) | 61 (10%) |
| 600 mg bid | 16 (16%) | 30 (4.8%) |
| 800 mg bid | 15 (15%) | 16 (2.5%) |

The "Number" indicates the number of AFib episodes greater than 6 minutes for all tested patients over the trial period (4 weeks for based line, 2 weeks experimental). The "Duration" in hours indicates the cumulative duration in hours over the trial period that the tested patients were measured in episodes of AFib greater than 6 minutes. The above results demonstrate that not only does budiodarone reduce the number of episodes of long duration AFib, but also reduces short episodes of AFib, thereby providing further protection against stroke and heart failure and significantly reducing the AFib burden.

For patients with paroxysmal and persistent AFib with high CHA2DS2-VASc scores (3 or higher), AFib episodes of greater than 6 minutes can lead to an increased risk of stroke and/or congestive heart failure. The data in Table 7 evidence that, for all doses of budiodarone tested, the number of episodes of AFib longer than 6 minutes were reduced significantly, and at high concentrations of 600 mg bid or 800 mg bid, these episodes were reduced by more than 80%.

Table 8 provides a summary of the fraction of time and the number of hours per week that the patients were in episodes of AFib greater than 6 minutes in duration, on average. The percent time in AFib was reduced by 90% for doses of budiodarone at 600 mg bid and 800 mg bid.

TABLE 8

| Episodes of AFib > 0.1 hrs | Fraction of hours (percent) | Duration in hrs/week (average per patient) |
|---|---|---|
| Off Drug (baseline) | 616/4032 (15%) | 25.2 |
| 200 mg bid | 71/2016 (3.5%) | 5.9 |
| 400 mg bid | 61/2016 (3.0%) | 5 |
| 600 mg bid | 30/2016 (1.5%) | 2.5 |
| 800 mg bid | 16/2016 (0.8%) | 1.3 |

The percent time in AFib for a patient is a critical parameter that directly relates to risk factors for stroke and/or congestive heart failure, especially for patients with high CHA2DS2-VASc scores. In Table 8, there was a 76.7% drop in percent time in AFib for patients using 200 mg budiodarone twice a day, which further drops to 90% for patients using 600 mg budiodarone twice a day, and even further drops to 94.8% for patients using 800 mg budiodarone twice a day.

Example 7—Measurement of Longest Episodes of AFib During the Twelve Week Period

This example is a clinical trial evaluation of 6 patients treated with different doses of budiodarone each for a two-week period to determine the longest duration episode of AFib experienced at each dose. In this example, the patients' heart rhythms were continuously monitored over a twelve-week period with a pacemaker. The different doses and results of this evaluation are provided in Table 9 below:

TABLE 9

| 2 Weeks | Subject 1 | Subject 2 | Subject 3 | Subject 4 | Subject 5 | Subject 6 | Total |
|---|---|---|---|---|---|---|---|
| Baseline | 13 hrs | 16 hrs | 50 hrs | 5 hrs | 8 hrs | 35 hrs | 127 hrs |
| 200 mg bid | 5 hrs | 6 hrs | 7 hrs | 0 hrs | 3 hrs | 6 hrs | 21 hrs |
| 400 mg bid | 8 hrs | 13 hrs | — | 2 hrs | 2 hrs | 10 hrs | 33 hrs |
| 600 mg bid | 7 hrs | 0 hrs | — | 2 hrs | 0.8 hrs | 0 hrs | 7.8 hrs |
| 800 mg bid | 3 hrs | 5 hrs | — | 1 hr | 1.6 hrs | 3 hrs | 13.6 hrs |
| Washout | 105 hrs | 12 hrs | 8 hrs | 16 hrs | 2 hrs | 18 hrs | 161 hrs |

The above results evidence the variability of long duration AFib (when equal to or greater than 5 hours) in a patient treated with different doses of budiodarone. In Subjects 4 and 5, treatment with just 200 mg budiodarone twice a day was sufficient to eliminate all episodes of long duration AFib (>5 hrs) in these patients. However, Subject 1 required 800 mg bid budiodarone to eliminate all episodes of long duration AFib (>5 hrs) whereas Subject 6 required 600 mg budiodarone bid to eliminate all episodes of budiodarone. This data establishes how long term monitoring of a patient coupled with a dose adjustment of budiodarone is required to properly treat patients with paroxysmal or persistent AFib evidencing episodes of long duration AFib.

The results of Examples 2 to 7 establish that the use of an appropriate dose of budiodarone coupled with monitoring heart rhythms of treated patients allows for a reduction of all episodes of long duration AFib of greater than 5 hours coupled with a reduction in the overall AFib burden. This latter result evidences that a patient's progression from paroxysmal AFib to persistent AFib or from persistent AFib to permanent AFib can be reduced or prevented.

The administration of budiodarone according to the present method may be conducted using a pharmaceutical composition comprising from about 1% to 99% of budiodarone and the remainder being a pharmaceutically acceptable excipient, such as corn starch, cellulose, stearic acid, water, or other components. The pharmaceutical composition can be formulated into any form which, by way of example, only, may include one or more of a tablet, a capsule, a powder, and/or another formulation for oral administration; a parenteral administration, such as a solution suitable for one or more of intravenous administration, intramuscular administration, etc.; a suppository and/or enema; cutaneous and/or transdermal preparations, etc.

Example 8—Programming the Wearable

In an embodiment, the wearable may be programmable (e.g., by the clinician, the patient, and/or remotely, such as by the central analysis center). The wearable may be programmed to capture the patient's heart rhythm data. The data so generated can be interrogated and/or analyzed by the CPU on the wearable and/or can be transmitted to another device for interrogation and/or analysis. One example of programming of the wearable may enable the use of the wearable for monitoring the patient's heart rhythm and relaying the data directly and/or indirectly to, e.g., a clinician as follows.

A. A USER INTERFACE: Step functions for programming AFib monitoring system involving the wearable and relying on information through a network to the attending clinician.

B. The data collected is in a readable display for the clinician and other authorized individuals to access.

C. The readable display should be made available to the authorized clinician at all times, and only the authorized clinician should be authorized to save data and/or reset the monitoring system after going through one or more of Steps 1-15 below.

D. Drug exposure, dose, and/or any other medications taken by the patient can be retrieved as needed by the clinician from a patient's medical records, e.g., by integrating the monitoring system with the patient's medical records (e.g., electronic medical records).

E. Steps 1 to 14 are the only manual entry required, but step 14 is optimal and can be overridden by the clinician simply pushing Manual Reset Step 15.

F. All data may be saved after review by the attending clinician, who may also be authorized to program integration of prior observation periods (Step 17), whether on or off a pharmaceutical to treat AFib including budiodarone.

G. The system is user friendly, the attending clinician only needs to do 4 things each time: 1) enter patient or code to access data, 2) review data display, 3) enter dose of budiodarone in Step 14 if they wish, then 4) Push Manual Reset and Store Data.

H. The attending clinician has access to the stored data and integrates observation periods to compare AFib characteristics on different doses of budiodarone or off-drug (Step 17).

Each of the steps are set forth in Table 10 below:

TABLE 10

| Step | Function or Desired Output | Units Displayed | Function Recorded |
|---|---|---|---|
| 1 | Patient Name or Code | Characters | Uncharged |
| 2 | Patient Age | Years | Unchanged |
| 3 | Observation Period | Numbers | 1-1000 |
| 3a | Observation Interval | Weeks | Minimum reset at least 1 week and preferably at least 2 weeks |
| 4 | % Time in AFib | % | 0-100% |
| 5 | Longest Episode | Hours | Continuous variable |
| 6 | Number of episodes > 24 hrs | Number | Continuous variable |
| 7 | Duration of episodes > 24 hrs | Hours | Continuous variable |
| 8 | Number of episodes > 5 hrs | Number | Continuous variable |
| 9 | Duration of episodes > 5 hrs | Hours | Continuous variable |
| 10 | Number of episodes > 1 hr | Number | Continuous variable |
| 11 | Duration of episodes > 1 hr | Hours | Continuous variable |
| 12 | Number of episodes > 0.1 hr | Number | Continuous variable |
| 13 | Duration of episodes > 0.1 hr | Hours | Continuous variable |
| 14 | Dose of Pharmaceutical (e.g., Budiodarone) | mg/day | Optional Entry by Clinician |
| 15 | Push Manual Reset and Save | — | Once |
| 16 | Entry Accessed in Saved Data | All Above | Unlimited |
| 17 | Integration of Saved Data | Periods #'s | Unlimited |

Each of Steps 4-13 may be included or excluded in the programming of the wearable (e.g., at the discretion of the clinician), provided that at least one of these steps is included. In one embodiment, Steps 4-7 may be performed, and the corresponding data collected, and one or more of Steps 8-13 may be excluded. In another embodiment, Steps 4, 5, 8, and 9 may be included, and Steps 5, 6, and 10-13 may be excluded. In another embodiment, Steps 4, 5, 10, and 11 may be included, and steps 6, 7, 8, 9, 12, and 13 may be excluded. In yet another embodiment, Steps 4, 5, 12, and 13 may be included and Steps 6-11 may be excluded.

In still another embodiment, the attending clinician may program the wearable according to one or more of Steps 4-13.

Embodiments

Provided below are certain embodiments.

Embodiment I-1. A method to assess whether a patient with either paroxysmal or persistent atrial fibrillation (AFib) qualifies for a budiodarone therapy, the method comprising:
　a) selecting a patient afflicted with paroxysmal or persistent AFib;
　b) fitting said patient with a wearable, wherein said wearable comprises:
　　i) at least one of an electrode or an optical sensor, wherein the at least one of the electrode or the optical sensor is configured to, when the wearable is fitted on the patient, continuously or semi-continuously monitor a heart rhythm of the patient;
　　ii) a first computing device configured to collect and store heart rhythm data based on the monitored heart rhythm; and
　　iii) a transmission component configured to transmit data based on the heart rhythm data in the first computing device to a second computing device accessible by a clinician;
　c) causing transmission of the data to the second computing device, wherein the data indicates at least one of a presence of a long duration episode of AFib, an absence of a long duration episode of AFib, a number of long duration episodes of AFib, and optionally an extent of AFib burden; and
　d) qualifying said patient for budiodarone therapy based on a determination that the data satisfies at least one of a threshold number of long duration episodes of AFib and/or a threshold AFib burden.

Embodiment I-2. The method of embodiment I-1, wherein the first computing device is configured to determine the data based on the heart rhythm data by evaluating the stored heart rhythm data to determine the presence of a long duration episode of AFib and the number of long duration episodes of AFib.

Embodiment I-3. The method of embodiment I-2, wherein said evaluating is continuous.

Embodiment I-4. The method of any of embodiment I-2 or embodiment I-3, wherein said evaluating is also, or alternatively, semi-continuous.

Embodiment I-5. The method of any of embodiments I-1 to I-4, wherein the first computing device is programmed to, based on the data, alert at least one of the clinician or the patient of a detected long-duration episode of AFib that places the patient at risk of stroke.

Embodiment I-6. The method according to any of embodiments I-1 to I-5, wherein the qualifying said patient for budiodarone therapy comprises determining, based on the data, that the patient meets at least one of the following criteria:
 a) at least one AFib episode of at least 5 hours duration in a 30-day period or at least two episodes at least 1 hour in duration in a 30-day period coupled with an AFib burden at least 2.5% during the 30-day period;
 b) at least one AFib episode of at least 5 hours duration in a 30-day period or at least 2 episodes at least one hour in duration in a 30-day period coupled with an AFib burden at least 5% during the 30-day period;
 c) at least one AFib episode of at least 5 hours duration in a 30-day period coupled with an AFib burden at least 2.5% during the 30-day period;
 d) at least one AFib episode of at least 5 hours duration in a 30-day period coupled with an AFib burden at least 5% during the 30-day period;
 e) at least two AFib episodes of at least 1 hour in duration in a 30-day period coupled with an AFib burden at least 2.5% during the 30-day period; or
 f) at least two AFib episodes of at least 1 hour duration in a 30-day period coupled with an AFib burden at least 5% during the 30-day period.

Embodiment I-7. The method according to any of embodiments I-1 to I-6, wherein the wearable is one or more of a patch, a watch, a wristband, a strap, a ring, or a device that adheres to a body when fitted, and wherein the wearable is configured to measure the heart rhythm and transmit the heart rhythm data directly or indirectly to the second computing device.

Embodiment I-8. The method according to any of embodiments I-1 to I-7, wherein the patient is refractory to one or more other methods of treating AFib.

Embodiment II-1. A method of treating a patient diagnosed with either paroxysmal or persistent atrial fibrillation (AFib), the method comprising:
 administering budiodarone to the patient;
 wherein the patient was identified for budiodarone treatment based on:
 a to be identified patient being fit with a wearable, wherein said wearable comprises:
 at least one of an electrode or an optical sensor, wherein the at least one of the electrode or the optical sensor is configured to, when the wearable is fitted on said to be identified patient, continuously or semi-continuously monitors a heart rhythm of said to be identified patient;
 a first computing device configured to collect and store heart rhythm data based on the monitored heart rhythm of said to be identified patient; and
 a transmission component configured to transmit data based on the heart rhythm data of said to be identified patient in the first computing device to a second computing device accessible by a clinician;
 the data of said to be identified patient being transmitted to the second computing device, wherein the data indicated at least one of a presence of a long duration episode of AFib, an absence of any long duration episode of AFib, a number of long duration episodes of AFib, and optionally an extent of AFib burden; and
 a determination being made that the data satisfied at least one of a threshold number of long duration episodes of AFib and/or a threshold AFib burden; and
 wherein said patient identified for budiodarone treatment is determined to have budiodarone responsive AFib.

Embodiment II-2. The method of embodiment II-1, wherein the patient identified for budiodarone is refractory to one or more other methods of treating AFib.

Embodiment III-1. A method to assess if a qualified patient on budiodarone therapy should be dose adjusted for or disqualified from a budiodarone therapy, the method comprising:
 a) selecting the qualified patient; wherein the qualified patient is:
 on budiodarone therapy comprising treatment with a dose of budiodarone or a pharmaceutical composition comprising budiodarone; and
 fitted with a wearable, wherein said wearable comprises:
 i) at least one of an electrode or optical sensor, wherein the at least one of the electrode or the optical sensor is configured to, when the wearable is fitted, continuously or semi-continuously monitor a heart rhythm of the qualified patient;
 ii) a first computing device configured to collect and store heart rhythm data based on the monitored heart rhythm; and
 iii) a transmission component configured to transmit data based on the heart rhythm data in the first computing device to a second computing device accessible by a clinician;
 c) causing collection and transmission of the heart rhythm data to the second computing device, wherein the second computing device is configured to evaluate the heart rhythm data for a presence and a number of long duration episodes of AFib and an extent of AFib burden;
 d) optionally adjusting the dose of budiodarone to assess an appropriate dose for that patient; and
 e) assessing whether the collected heart rhythm data that the patient is responsive, is partially responsive, or is not responsive to budiodarone therapy;
 wherein said therapy is maintained for responsive patients, adjusted for partially responsive patients, and further wherein said therapy is terminated for non-responsive patients.

Embodiment III-2. The method of embodiment III-1, wherein said dose of budiodarone is at least about 200 mg twice a day.

Embodiment III-3. The method according to any of embodiments III-1 to III-2, wherein said dose of budiodarone is from about 200 mg twice a day to about 800 mg twice a day.

Embodiment III-4. The method of embodiment III-3, wherein said dose of budiodarone is selected from about 200 mg twice a day, about 400 mg twice a day, 600 mg twice a day, and about 800 mg twice a day.

Embodiment III-5. The method according to any of embodiments III-1 to III-4, wherein budiodarone is administered as a pharmaceutical composition.

Embodiment III-6. The method according to any of embodiments III-1 to III-5, wherein said monitoring with the wearable is maintained for the responsive patients to confirm that said patients remain responsive.

Embodiment III-7. The method of embodiment III-6, wherein said patients who are initially responsive to budiodarone but who later become non-responsive are dose adjusted with budiodarone provided that if said dose adjustment fails to restore the patient budiodarone responsive, the patient is removed from treatment with budiodarone.

Embodiment III-8. The method according to any of embodiments III-1 to III-7, wherein said responsive patients are placed in a registry that identifies those patients as eligible for treatment with budiodarone wherein a listing in the registry is a requirement for receiving budiodarone.

Embodiment III-9. The method according to any of embodiments III-1 to III-8, wherein the data generated by the wearable is transmitted directly or indirectly to a clinician who can assess a presence or an absence of long duration AFib and optionally the extent of AFib burden to the patient.

Embodiment III-10. The method of embodiment III-9, wherein said data is initially transmitted to a remote laboratory where a qualified health care professional analyzes the data.

Embodiment III-11. The method of embodiment III-10, wherein said qualified health care professional confirms that the patient is eligible for treatment with budiodarone and provides, to an attending information, information indicating:
that said professional has confirmed that the patient is eligible; and
one or more of the data or the analysis made by said professional.

Embodiment III-12. The method according to any of embodiments III-10 to III-11 wherein said qualified health care professional determines whether a patient responsive to treatment with a given dose of budiodarone remains responsive; and
if said qualified health care professional determines that said patient is now non-responsive, said professional provides said determination to an attending clinician, with one or more of:
a recommendation to dose adjust the patient to restore the patient's responsiveness; or
a recommendation to terminate the patient's treatment with budiodarone if said now non-responsive patient is being treated with a maximum prescribed dose.

Embodiment III-13. The method according to any of embodiments III-1 to III-12, wherein the assessing the collected heart rhythm data comprises assessing the collected heart rhythm data that was collected beginning at least 3 days after either budiodarone administration was initiated or dose adjustment of budiodarone was initiated.

Embodiment III-14. The method according to any of embodiments III-1 to III-13, wherein the assessing the collected heart rhythm data comprises assessing the collected heart rhythm data that was collected beginning at least 14 days after either budiodarone administration is initiated or dose adjustment of budiodarone is initiated.

Embodiment IV-1. A method for reducing a risk of a patient progressing from paroxysmal AFib to persistent AFib or from persistent AFib to permanent AFib, which method comprises:
identifying a patient with either paroxysmal or persistent AFib having a AFib burden of at least 2.5% coupled with at least one episode of long duration AFib over a 4-week period; administering budiodarone to said patient at a dose;
monitoring efficacy of said administration and optionally adjusting the dose as needed to achieve a reduction in either or both of AFib burden and long duration AFib, whereupon the risk of progression from paroxysmal AFib to persistent AFib or from persistent AFib to permanent AFib is reduced by said dose adjustment; and
maintaining said patient monitoring to confirm continued efficacy of budiodarone.

Embodiment IV-2. The method of embodiment IV-1, wherein the method also, or alternatively, comprises one or more of:
assessing whether the patient qualifies for a budiodarone therapy according to any of embodiments I-1 to I-8;
treating the patient according to any of embodiments II-1 to II-2; or assessing whether the patient should be dose adjusted for or disqualified from budiodarone therapy according to any of embodiments III-1 to III-14.

Embodiment V-1. A method for reducing a risk of heart failure in a patient diagnosed with paroxysmal AFib or persistent AFib, which method comprises:
identifying a patient with either paroxysmal or persistent AFib having an AFib burden of at least 2.5% coupled with at least one episode of long duration AFib over a 4-week period;
administering budiodarone to said patient at a dose;
monitoring efficacy of said dose administration and optionally adjusting the dose to achieve a reduction in either or both of AFib burden and long duration AFib, whereupon the risk of heart failure in said patient is reduced; and maintaining said patient monitoring to confirm continued efficacy of budiodarone.

Embodiment V-2. The method of embodiment V-1, wherein the method also, or alternatively, comprises one or more of:
assessing whether the patient qualifies for a budiodarone therapy according to any of embodiments I-1 to I-8;
treating the patient according to any one of embodiments II-1 to II-2; or assessing whether the patient should be dose adjusted for or disqualified from budiodarone therapy according to any of embodiments III-1 to III-14.

Embodiment VI-1. A method for reducing a risk of stroke in a patient diagnosed with paroxysmal AFib or persistent AFib, which method comprises:
identifying a patient with either paroxysmal or persistent AFib having an AFib burden of at least 2.5% coupled with at least one episode of long duration AFib over a 4-week period; administering budiodarone to said patient at a dose;
monitoring efficacy of said administration and optionally adjusting the dose as needed to achieve a reduction in either or both of AFib burden and long duration AFib whereupon the risk of stroke in said patient is reduced; and
maintaining said patient monitoring to confirm continued efficacy of budiodarone.

Embodiment VI-2. The method of embodiment VI-1, wherein the method also, or alternatively, comprises one or more of:
  assessing whether the patient qualifies for a budiodarone therapy according to any of embodiments I-1 to I-8;
  treating the patient according to any one of embodiments II-1 to II-2; or assessing whether the patient should be dose adjusted for or disqualified from budiodarone therapy according to any of embodiments III-1 to III-15.

Embodiment VII-1. A method to treat a patient with paroxysmal or persistent AFib, wherein said patient is refractory to one or more prior methods to treat AFib, which method comprises:
  a) selecting a patient who is refractory to the one or more prior methods to treat AFib;
  b) identifying a number of episodes of long duration AFib and an extent of AFib burden in the patient;
  c) qualifying the patient for a budiodarone treatment at a dosage based on the number of episodes of long duration AFib and the extent of AFib burden;
  d) fitting said patient with a wearable, wherein said wearable comprises:
    i) at least one of an electrode or an optical sensor, wherein said at least one of the electrode or the optical sensor, when the wearable is fitted on the patient, continuously or semi-continuously monitor a heart rhythm of the patient;
    ii) a first computing device configured to collect and store heart rhythm data based on the monitored heart rhythm of the patient; and
    iii) a transmission component configured to be able to transmit data based on the heart rhythm data in the first computing device to a second computing device accessible by a clinician;
  e) causing collection and transmission of the data based on the heart rhythm data to the second computing device, where the data is evaluated for a presence and number of long duration episodes of AFib and the extent of AFib burden;
  f) optionally adjusting dosing of budiodarone for the patient to assess an appropriate dose for the patient; and
  g) assessing whether the collected heart rhythm data evidence that the patient is responsive or is non-responsive to budiodarone therapy;
  wherein said therapy is maintained for responsive patients and wherein said therapy is terminated for non-responsive patients.

Embodiment VII-2. The method of embodiment VII-1, wherein the method also, or alternatively, comprises one or more of:
  assessing whether the patient qualifies for a budiodarone therapy according to any of embodiments I-1 to I-8;
  treating the patient according to any one of embodiments II-1 to II-2; or
  assessing whether the patient should be dose adjusted for or disqualified from budiodarone therapy according to any of embodiments III-1 to III-15.

Embodiment VIII-1. A method for reducing a risk that a patient with paroxysmal AFib will transition into persistent AFib, which method comprises:
  identifying a patient with paroxysmal AFib having an AFib burden of at least 2.5% coupled with at least one episode of long duration AFib over a 4-week period;
  administering budiodarone to said patient at a dose;
  monitoring efficacy of said administration and optionally adjusting the dose as needed to achieve a reduction in either or both of AFib burden and long duration AFib whereupon the risk of said transition in said patient is reduced; and maintaining said monitoring the patient to confirm continued efficacy of budiodarone.

Embodiment VIII-2. The method of embodiment VIII-1, wherein the method also, or alternatively, comprises one or more of:
  assessing whether the patient qualifies for a budiodarone therapy according to any of embodiments I-1 to I-8;
  treating the patient according to any one of embodiments II-1 to II-2; or assessing whether the patient should be dose adjusted for or disqualified from budiodarone therapy according to any of embodiments III-1 to III-15.

Embodiment IX-1. A method for reducing a risk that a patient with persistent AFib will transition into permanent AFib, which method comprises:
  identifying a patient with persistent AFib having an AFib burden of at least 2.5% coupled with at least one episode of long duration AFib over a 4-week period;
  administering budiodarone to said patient at a dose;
  monitoring efficacy of said administration and optionally adjusting the dose as needed to achieve a reduction in either or both of AFib burden and long duration AFib, whereupon the risk of said transition in said patient is reduced; and maintaining said monitoring the patient to confirm continued efficacy of budiodarone.

Embodiment IX-2. The method according to embodiment IX-1, also, or alternatively, comprising one or more of:
  assessing whether the patient qualifies for a budiodarone therapy according to any of embodiments I-1 to I-8;
  treating the patient according to any one of embodiments II-1 to II-2; or assessing whether the patient should be dose adjusted for or disqualified from budiodarone therapy according to any of embodiments III-1 to III-15.

What is claimed is:

1. A method for inhibiting a patient progressing from paroxysmal atrial fibrillation (AFib) to persistent AFib or from persistent AFib to permanent AFib, which method comprises:
  for said patient who is qualified for and responsive to budiodarone therapy at a first dose of budiodarone:
    monitoring said patient over a period of at least 6 months to confirm continued responsiveness to said budiodarone therapy,
    wherein, if said patient becomes non-responsive to said first dose during said monitoring, said budiodarone therapy comprises increasing a dosage of budiodarone to a higher dose until said patient is responsive to the budiodarone therapy at said higher dose, otherwise said budiodarone therapy is maintained at said first dose, and
    wherein said monitoring is to confirm that said patient has been inhibited from progressing from either paroxysmal AFib to persistent AFib or from persistent AFib to permanent AFib.

2. The method of claim 1, wherein the monitoring is continuous or semi-continuous.

3. The method of claim 1, wherein said patient is qualified based on having an AFib burden of at least 2.5% coupled with at least one episode of long duration AFib over about a 4-week period prior to said budiodarone therapy.

4. The method of claim 1, wherein the monitoring is based on heart rhythm data measured via a wearable engaged by said patient.

5. The method of claim 1, wherein said monitoring confirms that said inhibition for said patient has resulted in reversion from persistent AFib to paroxysmal AFib or sinus heart rhythm, or from paroxysmal AFib to sinus heart rhythm.

6. A method for inhibiting a patient progressing from paroxysmal atrial fibrillation (AFib) to persistent AFib or from persistent AFib to permanent AFib, wherein said patient is refractory to one or more prior methods to treat AFib, which method comprises:
for said patient who is refractory to one or more prior methods to treat AFib and who is qualified for and responsive to budiodarone therapy at a first dose of budiodarone:
monitoring said patient over a period of at least 6 months to confirm continued responsiveness to said budiodarone therapy,
wherein, if said patient becomes non-responsive to said first dose during said monitoring, said budiodarone therapy comprises increasing a dosage of budiodarone to a higher dose until said patient is responsive to the budiodarone therapy at said higher dose, otherwise said budiodarone therapy is maintained at said first dose, and
wherein said monitoring is to confirm that said patient has been inhibited from progressing from either paroxysmal AFib to persistent AFib or from persistent AFib to permanent AFib.

7. The method of claim 6, wherein the monitoring is continuous or semi-continuous.

8. The method of claim 6, wherein said patient is qualified based on having an AFib burden of at least 2.5% coupled with at least one episode of long duration AFib over about a 4-week period prior to said budiodarone therapy.

9. The method of claim 6, wherein the monitoring is based on heart rhythm data measured via a wearable engaged by a patient.

10. The method of claim 6, wherein said monitoring confirms that said inhibition for said patient has resulted in reversion from persistent AFib to paroxysmal AFib or sinus heart rhythm, or from paroxysmal AFib to sinus heart rhythm.

11. A method for reducing a risk that a patient with paroxysmal atrial fibrillation (AFib) will transition into persistent AFib, which method comprises:
for said patient with paroxysmal AFib, wherein said patient is qualified for and responsive to budiodarone therapy at a first dose of budiodarone:
monitoring said patient over a period of at least 6 months to confirm continued responsiveness to said budiodarone therapy,
wherein, if said patient becomes non-responsive to said first dose during said monitoring, said budiodarone therapy comprises increasing a dosage of budiodarone to a higher dose until said patient is responsive to the budiodarone therapy at said higher dose, otherwise said budiodarone therapy is maintained at said first dose, and
wherein said monitoring is to confirm that said patient has been inhibited from progressing from either paroxysmal AFib to persistent AFib or from persistent AFib to permanent AFib.

12. The method of claim 11 wherein said patient is refractory to one or more prior methods to treat AFib.

13. The method of claim 11, wherein the monitoring is continuous or semi-continuous.

14. The method of claim 11, wherein said patient is qualified based on having an AFib burden of at least 2.5% coupled with at least one episode of long duration AFib over about a 4-week period prior to said budiodarone therapy.

15. The method of claim 11, wherein said monitoring confirms that said inhibition for said patient has resulted in reversion from paroxysmal AFib to sinus heart rhythm.

16. A method for reducing a risk that a patient with persistent atrial fibrillation (AFib) will transition into permanent AFib, which method comprises:
for said patient with persistent AFib, wherein said patient is qualified for and responsive to budiodarone therapy at a first dose of budiodarone:
monitoring said patient over a period of at least 6 months to confirm continued responsiveness to said budiodarone therapy,
wherein, if said patient becomes non-responsive to said first dose during said monitoring, said budiodarone therapy comprises increasing a dosage of budiodarone to a higher dose until said patient is responsive to the budiodarone therapy at said higher dose, otherwise said budiodarone therapy is maintained at said first dose, and
wherein said monitoring is to confirm that said patient has been inhibited from progressing from either paroxysmal AFib to persistent AFib or from persistent AFib to permanent AFib.

17. The method of claim 16, wherein said patient is refractory to one or more prior methods to treat AFib.

18. The method of claim 16, wherein the monitoring is continuous or semi-continuous.

19. The method of claim 16, wherein said patient is qualified based on having an AFib burden of at least 2.5% coupled with at least one episode of long duration AFib over about a 4-week period prior to said budiodarone therapy.

20. The method of claim 16, wherein said monitoring confirms that said inhibition for said patient has resulted in reversion from persistent AFib to paroxysmal AFib or sinus heart rhythm.

* * * * *